United States Patent [19]

Leonard

[11] Patent Number: 4,994,449
[45] Date of Patent: Feb. 19, 1991

[54] METHOD FOR INCREASING BONE DENSITY IN HUMANS

[75] Inventor: Walter G. Leonard, Melrose, Mass.

[73] Assignee: Modulus III, Inc., Redding, Conn.

[21] Appl. No.: 443,089

[22] Filed: Nov. 27, 1989

Related U.S. Application Data

[63] Continuation of Ser. No. 179,963, Apr. 11, 1988, abandoned, which is a continuation-in-part of Ser. No. 764,945, Aug. 12, 1985, Pat. No. 4,736,849, which is a continuation-in-part of Ser. No. 563,148, Dec. 19, 1983, Pat. No. 4,534,468.

[51] Int. Cl.$^5$ .................. A61K 31/56; A61K 33/10
[52] U.S. Cl. .................................. 514/171; 514/170; 424/687
[58] Field of Search ........................... 514/170, 171

[56] References Cited

U.S. PATENT DOCUMENTS

| | | | |
|---|---|---|---|
| 3,409,721 | 11/1968 | Applezweig | 424/7.1 |
| 3,932,635 | 1/1976 | Segre | 514/170 |
| 3,939,264 | 2/1976 | Lachnit-Fixson | 514/170 |
| 3,942,641 | 3/1976 | Segre | 514/170 |
| 3,957,982 | 5/1976 | Lachnit-Fixson et al. | 514/170 |
| 3,969,502 | 7/1976 | Lachnit-Fixson | 514/170 |
| 4,530,839 | 7/1985 | Pasquale | 514/171 |
| 4,534,468 | 8/1985 | Nuckols et al. | 206/534 |
| 4,616,006 | 10/1986 | Pasquale | 514/170 |
| 4,621,079 | 11/1986 | Lachnit-Fixson et al. | 514/170 |
| 4,628,051 | 12/1986 | Pasquale | 514/170 |
| 4,736,849 | 4/1988 | Leonard et al. | 206/534 |

OTHER PUBLICATIONS

Utian WH. Overview on Menopause, Am. J. Obstet Gynecol., 1987; 56: 1280-1283.

Ettinger, B., Overview of the Efficacy of Hormonal Replacement Therapy, AM J. Obstet. Gynecol., 1987; 56: 1298-303.

Riggs, B. L., Pathogenesis of Osteoporosis, AM. J. Obstet. Gynecol, 1987; 56: 1342-46.

Judd, H., Utian, W. H., Current Perspectives in the Management of the Menopausal and Postmenopausal Patient-Introduction: What We Hope to Learn, Am. J. Obstet. Gynecol, 1987; 56: 1279-80.

Lindsay, R., Estrogen Therapy in the Prevention and Management of Osteoporosis, Am. J. Obstet. Gynecol, 1987; 56: 1347-51.

Parfitt, Am. Quantum Concept of Bone Remodeling and Turnover: Implications for the Pathogenesis of Osteoporosis, Calif Tissue Int., 1979; 28: 1-5.

Lindsay, R., Aitken, J. M., Anderson, J. B., Hart, D. M., McDonald, E. B., Clark, A. C., Long-Term Prevention of Post-Menopausal Osteoporosis by Estrogen, Lancet 1976; 1: 1038-41.

Lindsay, R. Hart, D. M., Forrest, C., Baird, C., Prevention of Spinal Osteoporosis in Oophorectomized Women, Lancet 1980; 2: 1151-4.

Ravnikar, V. A., Compliance with Hormone Therapy, Am. J. Obstet. Gynecol, 1987; 56: 1332-34.

Genant H. K., Cann, C. E., Ettinger, B, Gordon, G. S., Quantitative Computed Tomography of Vertebral Spongiosa; a Sensitive Method for Detecting Early Bone Loss After Oophorectomy, Ann. Intern. Med., 1982; 97: 699-705.

Kolata, G., How Important is Dietary Calcium in Preventing Osteoporosis?, Science, 1986; 233: 519-20.

Barnes, D. M., Close Encounters with an Osteoclaust., Science, 1987; 236: 914-16.

Peck, W. A., Riggs, B. L., Bell, N. H., Physician's Resource Manual on Osteoporosis, Nat. Osteoporosis Found., 1987: 15-16.

Reinhold, W. D., Genant, H. K., Reiser, U. J., Harris, S. T., Ettinger, B., Bone Mineral Content in Early-Post- Primary Examiner—Shep K. Rose
Attorney, Agent, or Firm—Mattern, Ware, Stoltz & Fressola (List continued on next page.)

[57] ABSTRACT

A method of increasing the bone density of postmenopausal women employs a calendar-oriented regimen of estrogen, progesterone and calcium. Such a regimen may be dispensed from a calendar-oriented pill dispenser having numerical indicia identifying each pill-containing enclosure with a given calendar date.

26 Claims, 20 Drawing Sheets

OTHER PUBLICATIONS

–Menopausal and Postmenopausal Osteroporotic Women: Comparison of Measurement Methods, Radiol 1986; 160: 469–78.

Weissman, B. N., Women's Health: Osteoporosis: Radiologic and Nuclear Medicine Procedures, Nat. Con. on Women's Health, U.S. Dept. of Health and Human Services, Jul. 1986: 127–31.

Ott, S. M., Chesnut, III, C. H., Hanson, J. A., Kilcoyne, R. F., Murano, R., Lewellen, T. K., Comparison of Bone Mass Measurements Using Different Diagnostic Techniques in Patients with Postmenopausal Osteoporosis, Osteoporosis; Proc. Copenhagen Int. Sym. on Osteoporosis 1984; Jun. 3–8; 93–6.

Munk–Jensen, N., Pors Nielsen S., Obel, E. B., Bonne Eriksen, P. Reversal of Postmenopausal Vertebral Bone Loss by Oestrogen and Progestogen: a Double Blind Placebo Controlled Study, Brit. Med. Jour., Apr. 1988: 1150–1152.

Miller, P., Advances in Osteoporosis Management, Contemporary OB/GNY, Dec. 1988: 31–46.

No author, How Estrogen Protects C–V Health Unclear, OB Gyn News, Jan. 15–31, 1989; 16.

Wozney, J. M., Rosen, V., Celeste, A. J., Mitsock, L. M., Whitters, M. J., Kritz, R. W., Hewick, R. M., Wang, E. A., Novel Regulators of Bone Formation Molecular Clones and Activities, Science 242: 1528.

Ravnikar, Proper Duration of Estrogen Replacement is in Question, OB Gyn News, Jan. 15, 1989; 24: 17.

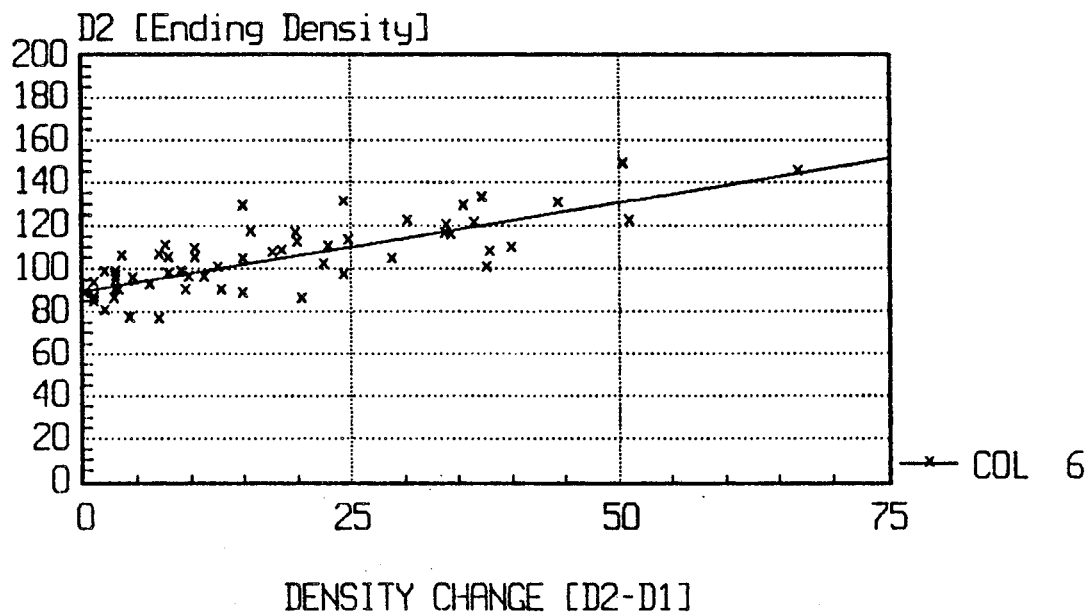
SLOPE ENDING DENSITY VS DENSITY CHANGE
Figure 14 [Table 6]
y=89.620861+0.8177759*x  r=0.781

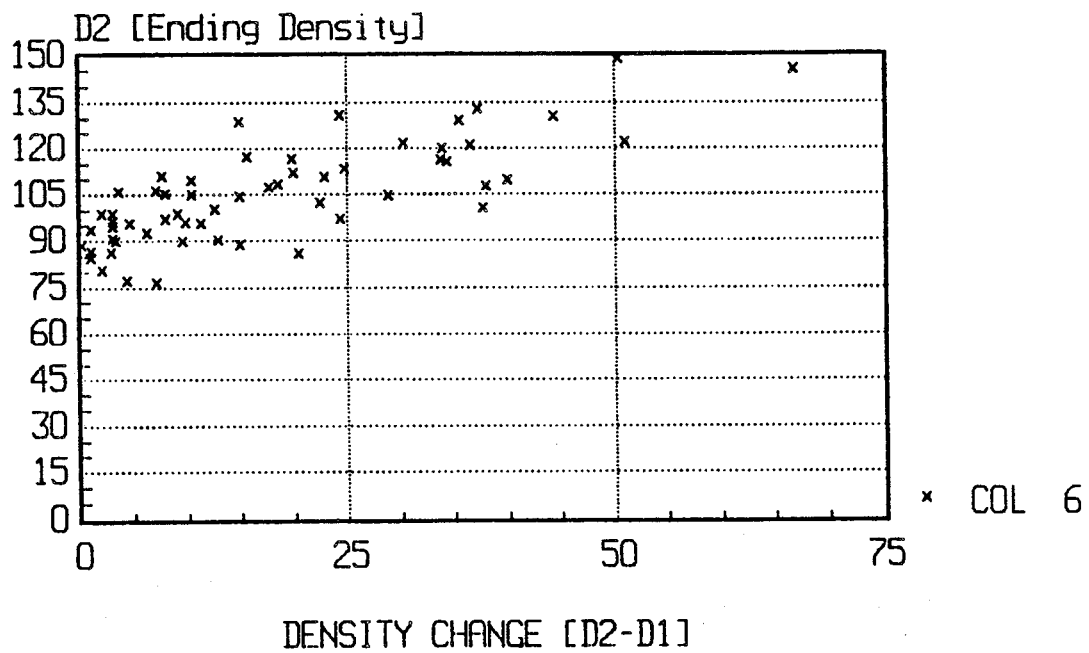

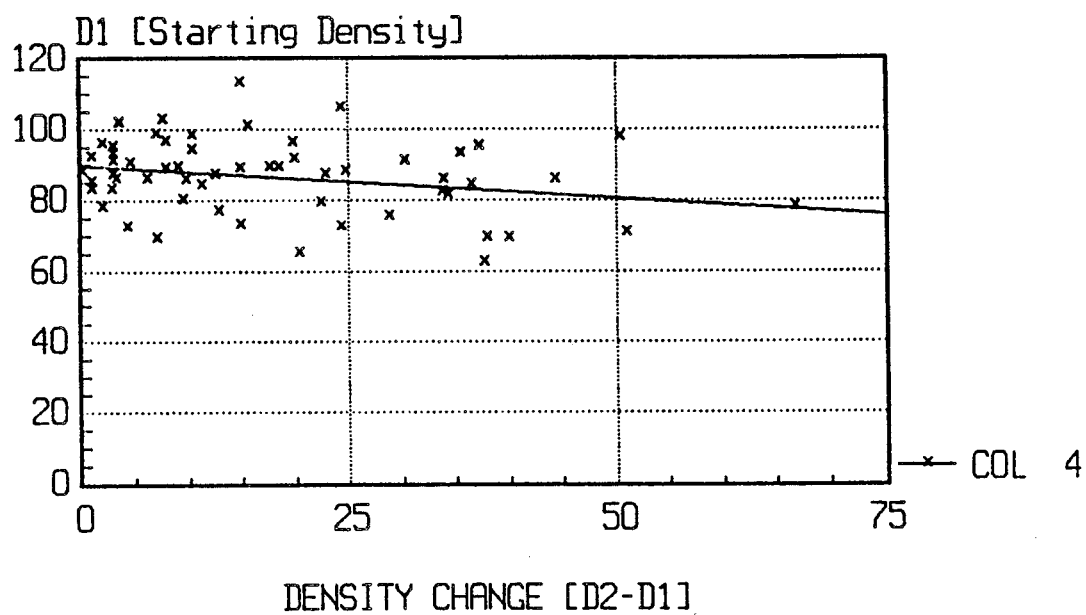

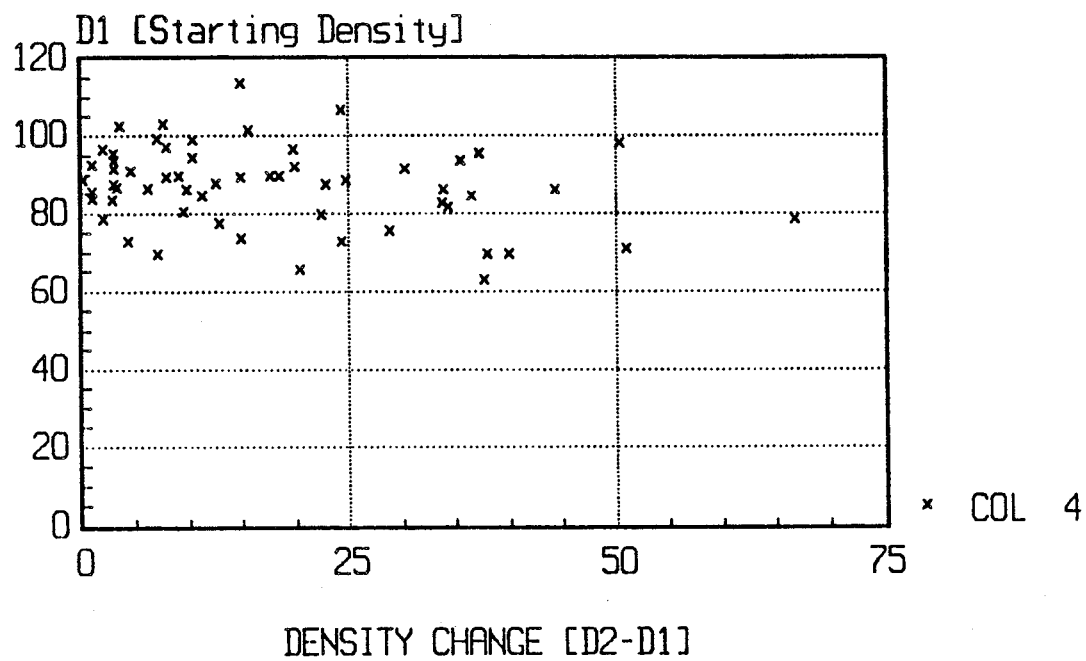

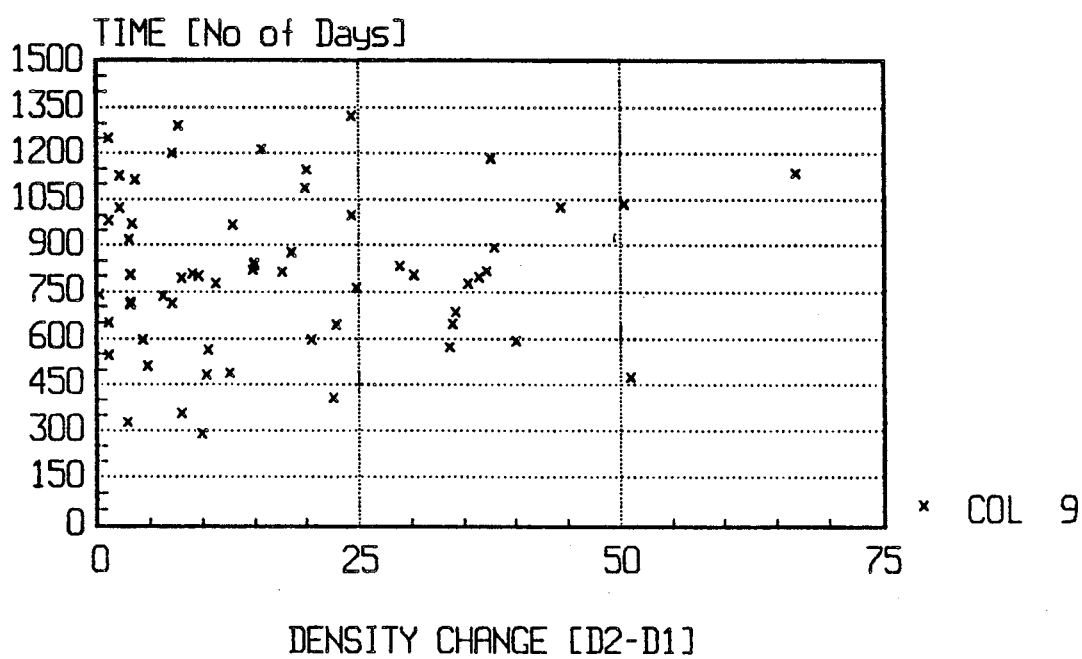

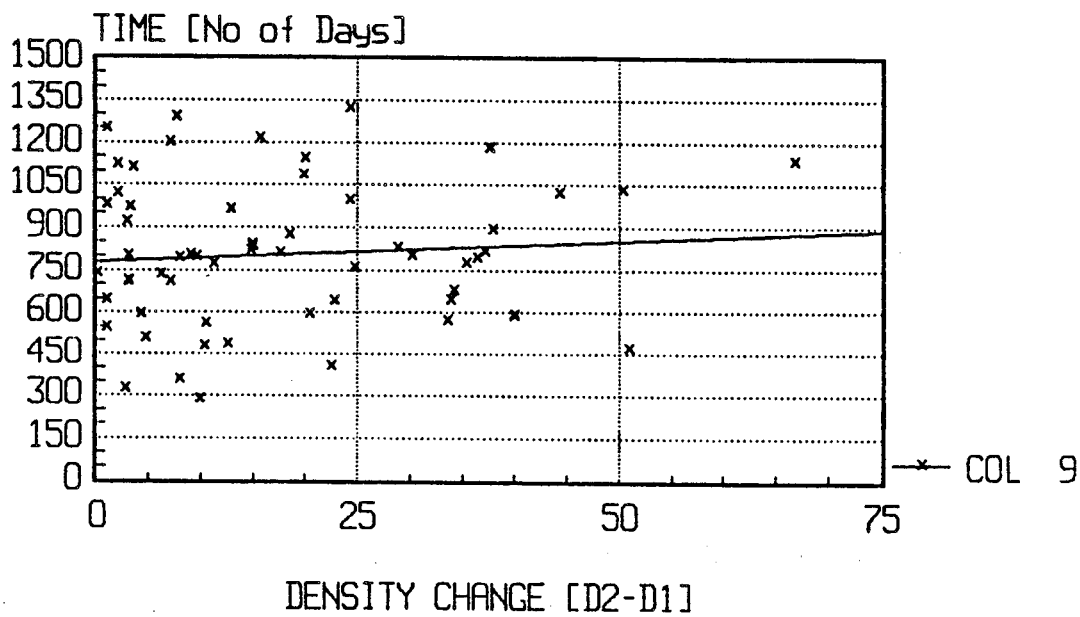

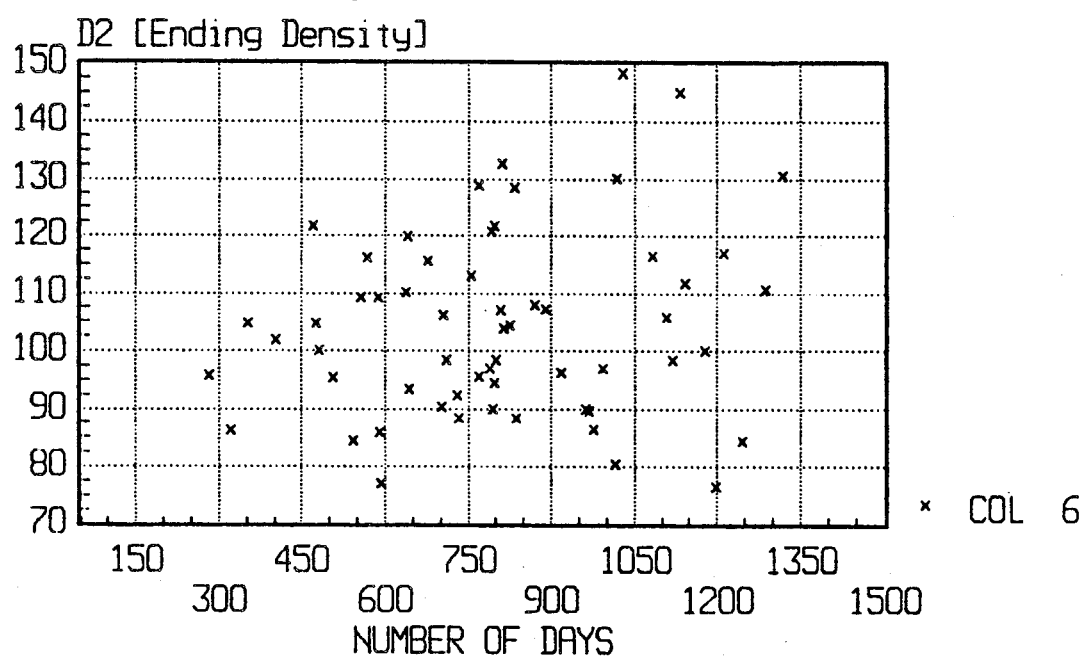

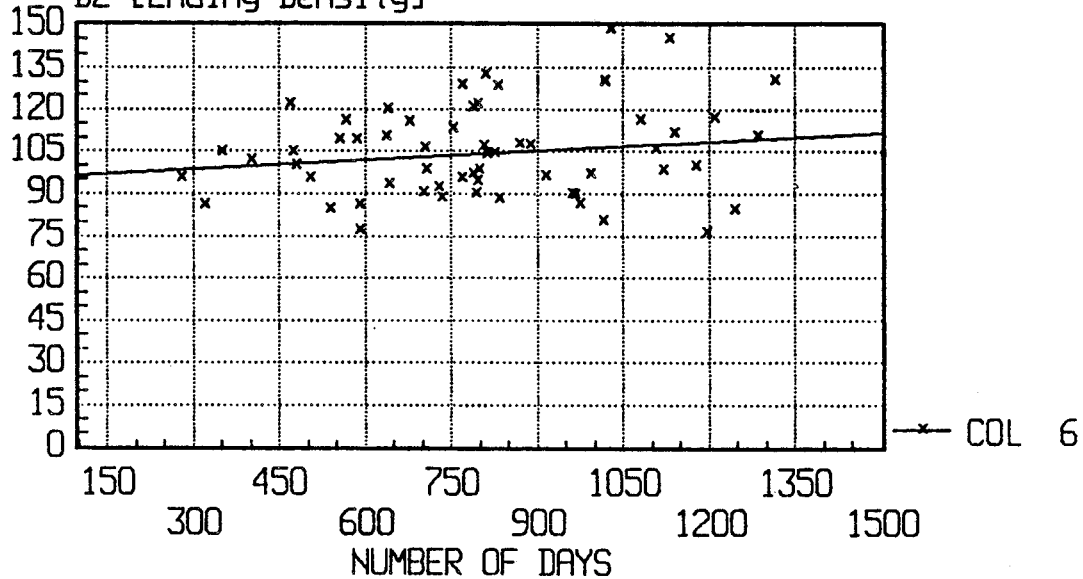

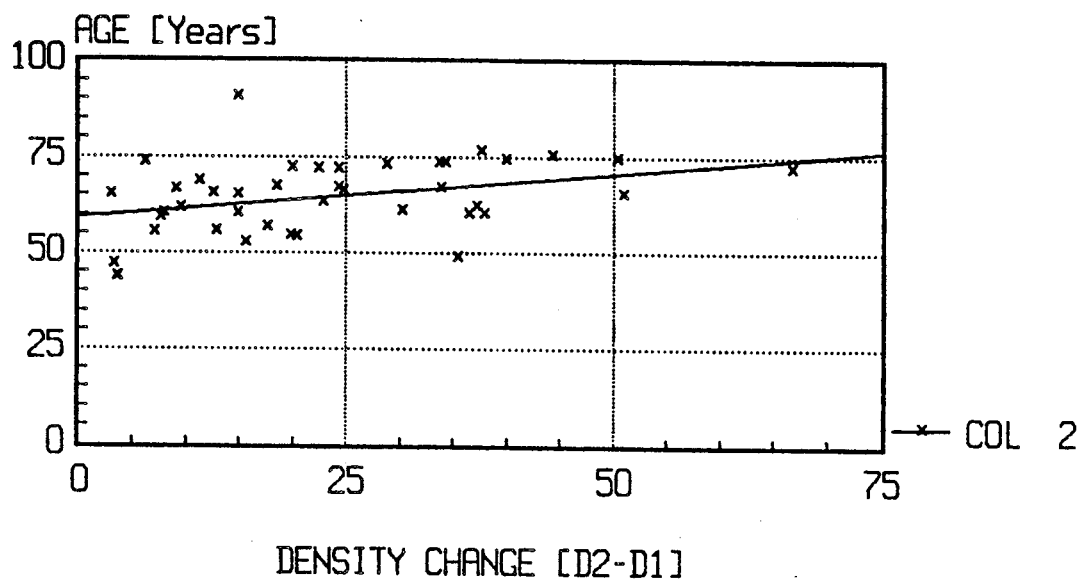

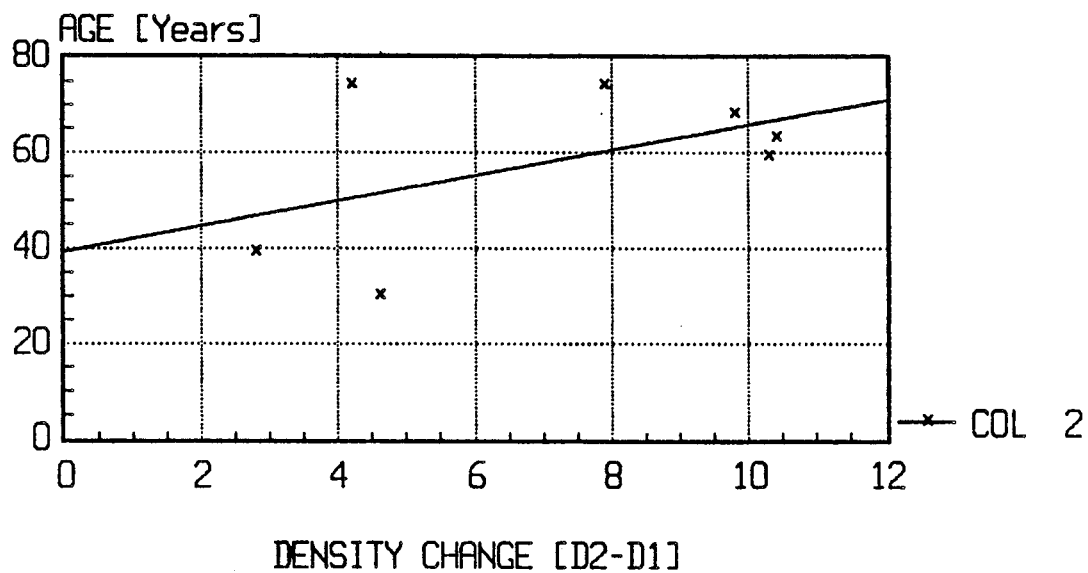

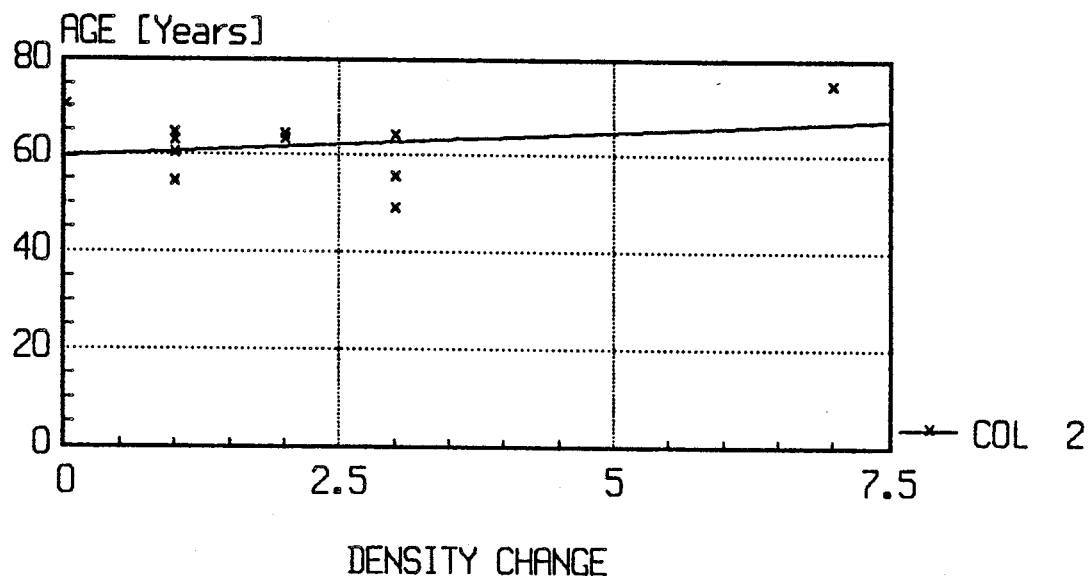

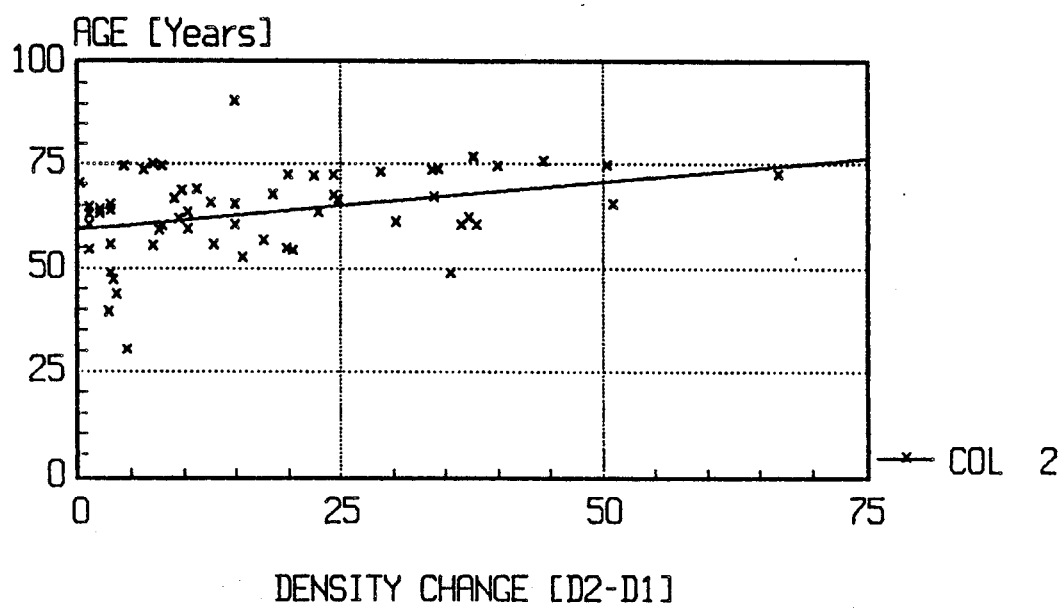

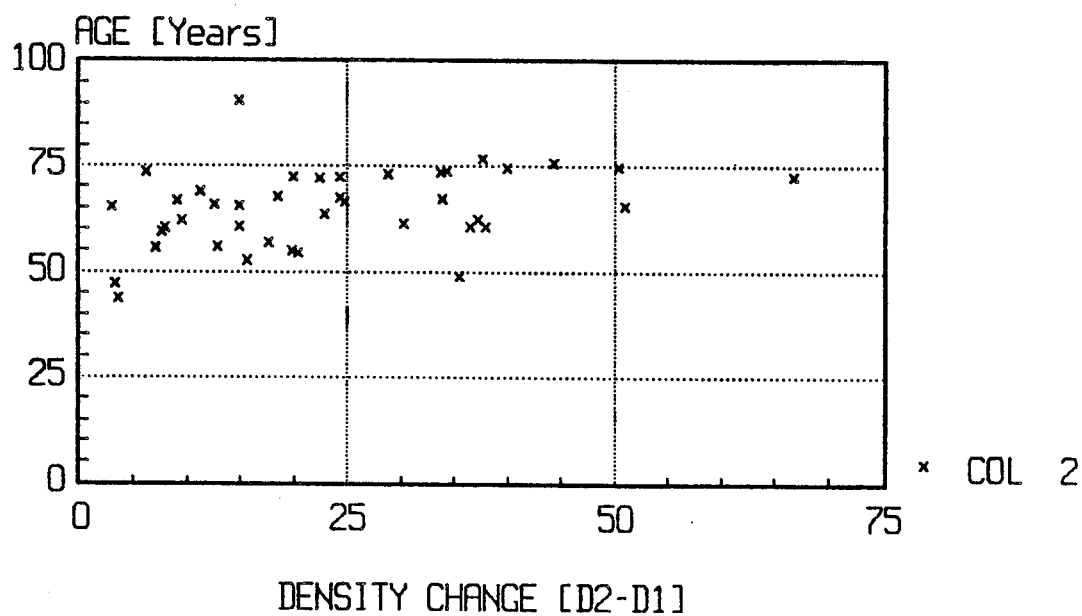

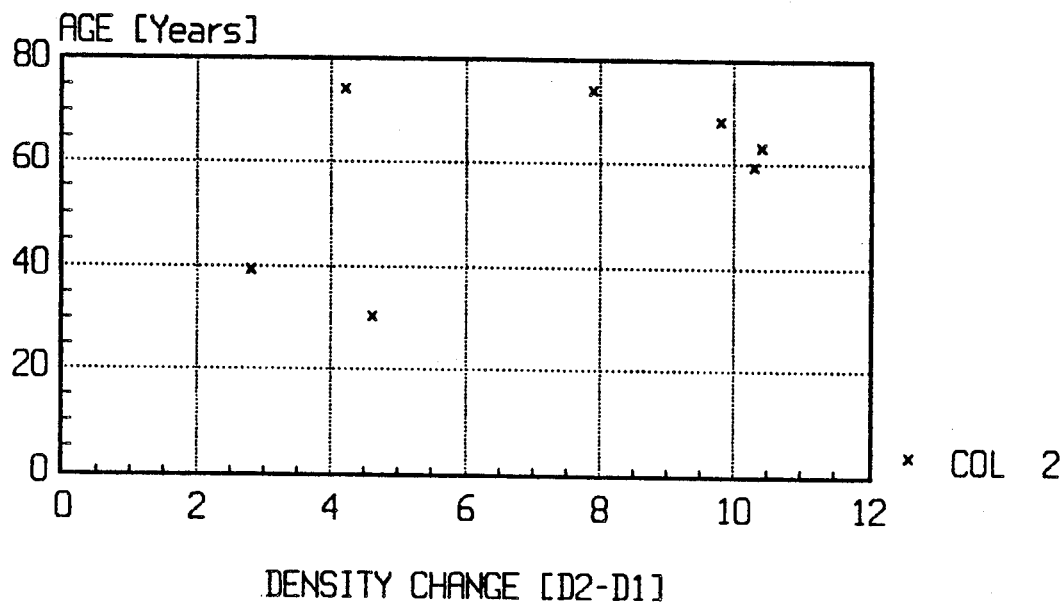

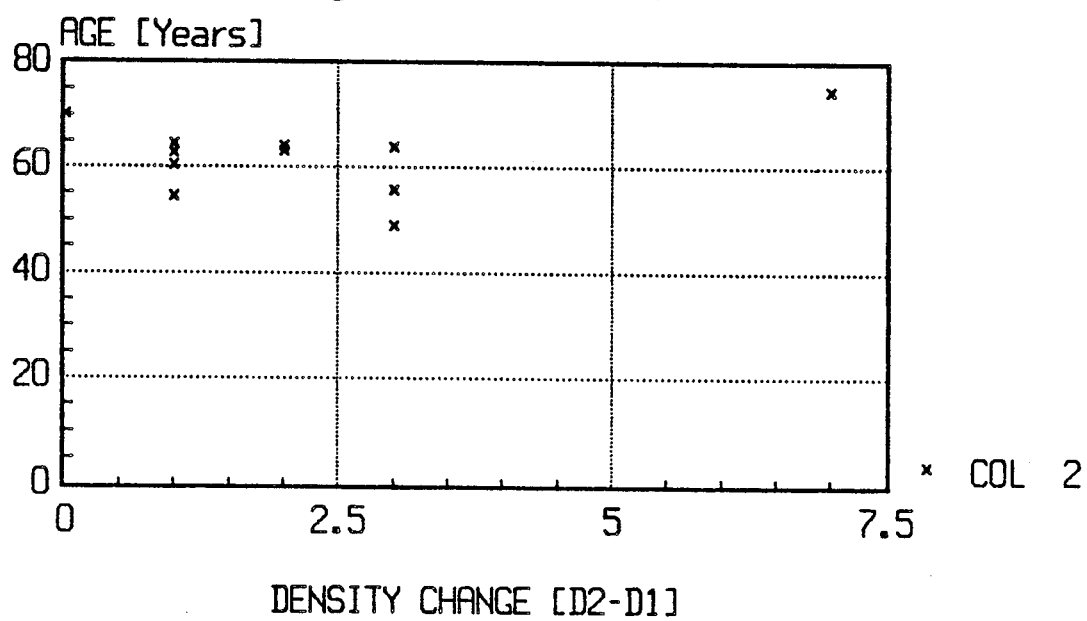

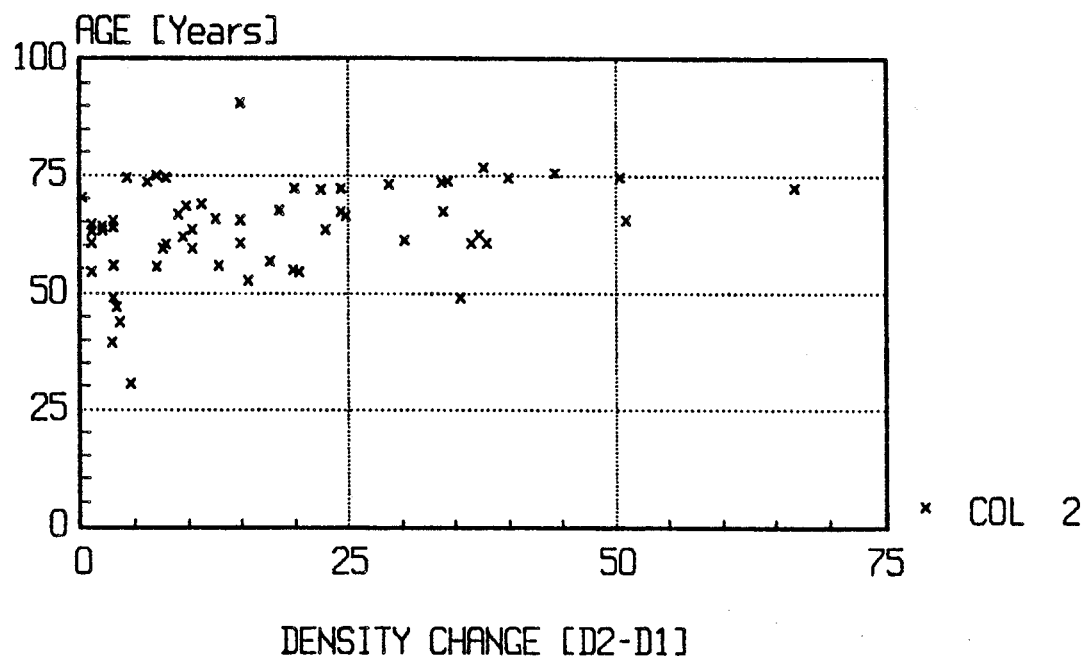

BONE DENSITOMETRY                                    PATIENT J.V.

SCAN: 1.5  12/8/86     ANALYSIS: 1.5  12/8/86

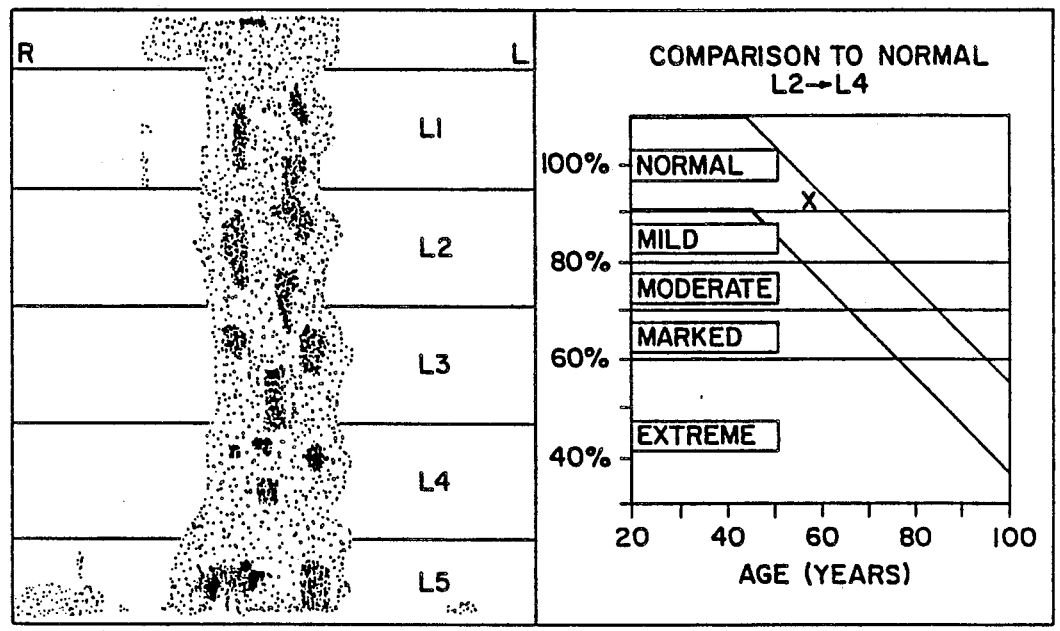

FIG. 6

| | | | | | |
|---|---|---|---|---|---|
| Age (years) | 57 | Large Standard | 18.10 | Scan Speed (mm/s) | 5.0 |
| Sex | Female | Medium Standard | 13.58 | Step Distance (mm) | 4.5 |
| Weight (lb) | 122.0 | Small Standard | 9.61 | Collimation (mm) | 13 |
| Height (in) | 62 | 44 KeV Air Value | 126410 | Corrected R value | 1.40 |
| Ethnic | White | 100 KeV Air Value | 106074 | | |

| REGION | BMD g/cm$^2$ | % Young Normal | % Age Matched | Fracture Risk |
|---|---|---|---|---|
| L1 | 1.129 | 95.9 | 115.2 | NORMAL |
| L2 | 1.210 | 96.2 | 114.1 | NORMAL |
| L3 | 1.160 | 92.2 | 109.4 | NORMAL |
| L4 | 1.101 | 87.5 | 103.8 | MILD |
| L1 -> L2 | 1.170 | 96.8 | 115.8 | NORMAL |
| L1 -> L3 | 1.166 | 95.0 | 113.2 | NORMAL |
| L1 -> L4 | 1.150 | 92.9 | 110.5 | NORMAL |
| L2 -> L3 | 1.183 | 94.0 | 111.6 | NORMAL |
| L2 -> L4 | 1.156 | 91.9 | 109.0 | NORMAL |
| L3 -> L4 | 1.132 | 90.0 | 106.8 | MILD |

METHOD FOR INCREASING BONE DENSITY IN HUMANS

CROSS-REFERENCE TO RELATED APPLICATIONS

This is a continuation of copending application Ser. No. 179,963filed on Apr. 11, 1988, now abandoned, which is a continuation-in-part application of U.S. Application Ser. No. 764,945, filed Aug. 12, 1985 for a Calendar-Oriented Pill Dispenser, now U.S. Pat. No. 4,736,849, issued Apr. 12,1988 which in turn is a continuation-in-part application of U.S. Pat. Application Ser. No. 563,148, filed Dec. 19, 1983 for a Calendar-Oriented Pill Dispenser, now U.S. Pat. No. 4,534,468.

TECHNICAL FIELD

The present invention relates to a method of increasing the bone density in humans and in particular, to increasing the bone density in post-menopausal women.

BACKGROUND OF THE INVENTION

It is well known that women at the onset of menopause, whether such onset occurs naturally or as a result of oophorectomy, develop a number of symptoms including hot flushes, vaginal atrophy, depression, anxiety, and nervousness[1,2] (*footnotes listed in Table* 11) as well as a decrease in bone density which is defined as osteoporosis if the absolute decrease in bone density reaches a point at which fractures begin to occur.[3] As reported in a recent article concerning the post-menopausal patient:[4]

"Of all the body systems that are at risk as women age, the skeletal system is one of most vulnerable because it is one of the systems most affected by the declining estrogen production".

Such decline in estrogen production occurs on the onset of menopause and continues throughout a woman's post-menopausal life. The symposium referred to in reference 4 entitled "Current Perspectives in the Management of the Menopausal and Post-Menopausal Patient" (Sept. 25-26, 1986 at Banff, Alberta, Canada) discussed various means of managing menopausal and post-menopausal symptoms, including the use of estrogen replacement therapy to counteract the problems associated with menopause.

Estrogen therapy replacement as noted in the literature[5] is believed to be most effective with an oral dose of conjugated equine estrogens of 0.625 mg/day, with such therapy beginning early in the post-menopausal period. Such treatment has been found effective in the prevention of osteoporosis with reduction in the incidence of vertebral fracture by approximately 90% and of hip fracture by approximately 50%.[5]

As further noted in the literature[5], low bone mass is an important factor in fracture risk and is related to two factors; namely (1) the amount of bone mass developed as a person matures and (2) accelerated bone loss after the menopause or oophorectomy. It is further noted that the post-menopausal acceleration of bone loss occurs at all skeletal sites and is characterized by loss of trabecular bone which in advanced states, produces significant changes in the architecture of the skeleton, including kyphosis (rounded shoulders and the ribs resting on the iliac crest) with chronic back pain and significant loss of height.[5] Trabecular bone is the honeycombed type bone generally found in the interior regions of a bone. Cortical bone is the denser type bone generally found in the outer regions of a bone.

The literature states that the treatment of osteoporosis is difficult in that once a patient has bone loss, no treatment can restore normal bone architecture and even restitution of bone mass will not change the women's body configuration.[5] Thus although estrogen replacement therapy instituted during the accelerated bone loss phase of menopause may recoup a small amount of bone mass[6,7,8], such recoupment is believed to be the filling in of the remodeling space that becomes enlarged during this phase of accelerated bone loss.[5] In addition, it has been the belief of physicians specializing in this field that estrogen therapy replacement gives better results in terms of maintaining bone mass the earlier it is introduced following the onset of menopause.[5]

Estrogen therapy has also been demonstrated to reduce cortical bone loss if administered immediately after the onset of menopause.[5]

It has also been discovered that cessation of therapy causes bone loss to resume, especially trabecular bone.[2,5] This acceleration tends to be of the same degree as that seen during the immediate post-menopausal phase. Thus it has been noted that the judicious use of estrogen therapy can reduce the fracture incidence in older women.[5] It is however conceded that the particular mechanism of action with regard to estrogen in reducing bone loss is not fully understood.[5]

A review of the medical literature indicates that no regimen is believed to increase bone density more than a few percentage points after onset of menopause and that at best, use of an estrogen therapy replacement regimen will, for most women, reduce bone loss but will not make any marked improvement in bone density, especially if such a treatment is initiated long after the onset of menopause.[2,5]

Furthermore, although the medical literature suggests that the use of progesterone in combination with estrogen may reduce the incidence of endometrial cancer[9] associated to some extent with estrogen treatment, no suggestion is made in the medical literature that the combination of estrogen with progesterone will increase bone density beyond the short-term increase in bone mass which may occur during the initial treatment of estrogen.[9]

A medical literature review of calcium supplementation indicates that the use of calcium alone in post-menopausal women may have limited effect in reducing bone loss, and that there is little data to support calcium supplementation as beneficial to post-menopausal women.[2,5,10] One study notes that there is no qualitative difference in bone loss between women with and without calcium supplementation of 1500 mg/day, although there is evidence that the dose of estrogen, if estrogen replacement therapy is prescribed, might be reduced in calcium replete women.[10]

Another article notes that two recent studies of post-menopausal women did not show any relationship between consumption of dietary calcium over a wide range of intake levels to rates of bone loss from the radius and lumbar spine.[11]

Applicant has conducted a study with seventy-nine post-menopausal women, the majority of whom showed signs of bone loss. This study has been conducted in conjunction with applicant Walter Leonard's calendar-oriented dispenser (U.S. Pat. No. 4,534,468 and U.S. application Ser. No. 764,945 now U.S. Pat. No. 4,736,849). This latter dispenser discloses a calendar regimen of 0.625 mg of conjugated estrogens for calendar days 1 through 25, 10 mg of medroxyprogesterone acetate for calendar days 16 through 25 and 500 mg calcium carbonate for calendar days 26 through the end of the month. It was believed that this regimen would be beneficial in treating the symptoms associated with menopause, and in view of the medical literature, was also believed to retard bone loss. It was not believed at the start of the study that this regimen would increase bone density in post-menopausal women.

The surprising result after tracking the women in the study for a period of approximately two years is that bone density increased for virtually all patients, and in many cases, bone density increased dramatically. More startling and unusual is the finding that the increase in bone density occurred independent of the patient's age at the onset of the regimen. Such a finding is in direct contradiction of using an estrogen regimen in post-menopausal women, as noted by B. Laurence Riggs of the Mayo Clinic in Rochester, Minn.[12] Indeed the data contained herein suggests that the amount of bone density increase is probably independent of the patient's age at the time of regimen onset; a finding which heretofore was believed contraindicated by the medical literature due to the known accelerated bone loss of the trabecular type bone following onset of menopause.

It is furthermore believed that the calendar-oriented nature of this regimen which includes the use of calcium supplementation following the first twenty-five days of the calendar regimen may be beneficial in a two-fold fashion; namely, (1) by increasing patient compliance through use of the calendar-oriented dispenser so that the cyclic starting day of the regimen corresponds to the first day of the calendar month; and (2) that the calcium supplementation may increase the blood level of calcium so as to make this substance more available for bone formation when needed due to the concomitant use of estrogens and progesterone.

Finally it is believed that the specific use of conjugated estrogens in combination with medroxyprogesterone acetate, rather than other forms of the estrogen and progesterone hormone may be therapeutic.

The discovery therefore is this particular drug regimen to increase bone density in post-menopausal women.

SUMMARY OF THE INVENTION

A method of increasing the bone density in humans has been discovered based upon use of a calendar-oriented regimen as disclosed in U.S. Pat. No. 4,534,468 and U.S. Pat. application Ser. No. 764,945. The particular regimen comprises the use of conjugated estrogen for calendar days 1 through 25, medroxyprogesterone acetate for calendar days 16 through 25, and calcium carbonate for calendar days 26 through the remaining days of the calendar month.

At the time of filing the application resulting in U.S. Pat. No. 4,534,468 and at the time of filing U.S. application No. 764,945, it was believed that a regimen of estrogen, progesterone and calcium would be effective in treating the symptoms associated with post-menopausal women. It was specifically stated therein that this regimen might help in reducing the amount of bone mass loss associated with post-menopausal women, but it was not believed at that time that the regimen would have any therapeutic effect with regard to increasing bone density of such women.

A relatively long-term study concerning the bone density of women treated with this regimen has been conducted by the applicant wherein the patient's bone density was measured at the initiation of the regimen and at approximately one to two years thereafter while the patient continued on the regimen.

The women selected for this study comprised post-menopausal women who showed potential signs of osteoporosis. From the seventy-nine people initially on the study, sixty-four have had their bone density retested following a period of from approximately one to two years in which they have taken the regimen through use of a pill dispenser as illustrated in U.S. Pat. No. 4,534,468 or as modified and as set forth in corresponding U.S. Application Ser. No. 764,945, filed Aug. 12, 1985 now U.S. Pat. No. 4,736,849. The results of these patients who were compliant with the regimen and not removed from the regimen due to complicating factors (such as use of cortisone) is dramatic since virtually all show an increase in bone density. This test data is even more unexpected in view of the fact that the increase in bone density occurs in patients regardless of their age at the time the regimen is initiated, a finding which was unexpected in view of the medical literature which indicated that bone loss retardation through the use of estrogen was most significant when such a regimen was initiated immediately after the onset of menopause.[2,12]

The specific drug regimen of these patients comprises 0.625 mg conjugated estrogen for calendar days 1–25, 10 mg medroxyprogesterone acetate for calendar days 16–25, and 500 mg calcium carbonate for calendar days 26 through the end of the calendar month.

Therefore the present invention is directed to this new use for the drug-regimen disclosed in applicant's U.S. Pat. No. 4,534,468 and applicant's co-pending application Ser. No. 764,945.

OBJECTS OF THE INVENTION

It is therefore a principal object of the present invention to provide a drug-regimen for increasing the bone density of post-menopausal women wherein the regimen comprises the calendar-oriented administration of conjugated estrogens, medroxyprogesterone, and calcium carbonate.

A further object of the present invention is to provide a method of increasing the bone density of post-menopausal women as described above, wherein for each calendar month conjugated estrogens are taken for calendar days 1 through 25, medroxyprogesterone acetate is taken for calendar days 16 through 25, and calcium carbonate is taken for the calendar day 26 through the end of the month.

A still further object of the present invention is to provide a method of increasing the bone density of post-menopausal women as described above, wherein the conjugated estrogens comprise 0.625 mg per daily dose, the medroxyprogesterone comprises 10 mg per daily dose, and the calcium carbonate comprises 500 mg per daily dose.

Another object of the present invention is to provide a method of increasing the bone density of post-menopausal women as described above, wherein the regimen is dispensed from a calendar-oriented dispenser having numerical indicia identifying each pill-containing enclosure as to the date it is to be dispensed.

A still further object of the present invention is to provide a method of increasing the bone density of post-menopausal women as described above wherein the pill-containing enclosures are arranged on a flat planar sheet and wherein the numerical indicia identifying each pill-containing enclosure are positioned on both the front and rear surfaces of the planar sheet or carrier sheets positioned over the planar sheet.

Other objects of the present invention will in part be obvious and will in part appear hereinafter.

BRIEF DESCRIPTION OF THE DRAWINGS

For a fuller understanding of the nature and objects of the present invention, reference should be made to the following detailed description taken in connection with the following drawings, in which:

FIG. 6 illustrates a typical data output graph associated with the dual photon absorptiometry method of measuring bone density.

FIG. 7 is a graphical representation of the data presented in Table 3 showing the change in bone density as a function of the patient's age.

FIG. 7A is a graphical representation of the data presented in Table 3A showing the change in bone density as a function of age for those patients having both bone density measurements made with radiographic absorptiometry.

FIG. 7B is a graphical representation of the data presented in Table 3B showing the change in bone density as a function of age for those patients having both bone density measurements made with dual photon absorptiometry.

FIG. 7C is a graphical representation of the data presented in Table 3C showing the change in bone density as a function of age for those patients having the first bone density measurement made with radiographic absorptiometry and the second measurement made with dual photon absorptiometry.

FIG. 8 is a graphical representation of the data presented in FIG. 7 using linear regression analysis.

FIG. 8A is a graphical representation of the data presented in FIG. 7A using linear regression analysis.

FIG. 8B is a graphical representation of the data presented in FIG. 7B using linear regression analysis.

FIG. 8C is a graphical representation of the data presented in FIG. 7C using linear regression analysis.

FIG. 9 is a graphical representation of the data presented in Table 4 showing the change in bone density as a function of the length of time each patient has been on the regimen.

FIG. 10 is a linear regression analysis of the data presented in FIG. 9.

FIG. 11 is a graphical representation of the data presented in Table 5 showing the change in bone density as a function of the starting density of each patient.

FIG. 12 is a linear regression analysis of the data presented in FIG. 11.

FIG. 13 is a graphical representation of the data in Table 6 showing the change in bone density as a function of the patient's ending density.

FIG. 14 is a linear regression analysis of the data presented in FIG. 13.

FIG. 15 is a graphical representation of the data presented in Table 4 showing the ending bone density of the patient (horizontal axis) as a function of the period of time that the patient was taking the regimen according to the present invention.

FIG. 16 is a linear regression analysis of the data presented in FIG. 15.

BEST MODE FOR CARRYING OUT THE INVENTION

Figure 5:
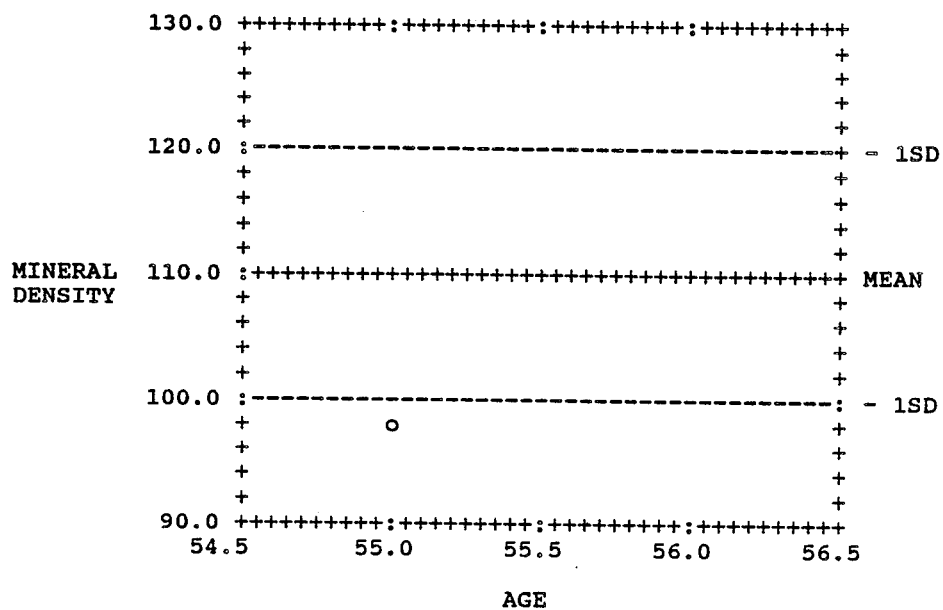
FIG. 5 illustrates a typical data output graph associated with the radiographic absorptiometry method of measuring bone density.

The present invention is directed to the new use of an estrogen-progesterone-calcium therapy replacement regimen. It is specifically directed to the treatment of osteoporosis by providing a regimen that increases he bone density in post-menopausal women.

Osteoporosis is generally defined as the loss of bone in post-menopausal women with a characteristic accelerated loss of trabecular bone up to the age of approximately sixty-five years and a steady but slower decrease in trabecular bone loss thereafter. Slow cortical bone loss begins after the age of approximately thirty-five and continues throughout the person's life. Trabecular bone is the honeycombed type bone generally found in the interior regions of a bone. Cortical bone is the denser type bone generally found in the outer regions of a bone.

In an article[2] by Dr. Bruce Ettinger entitled "Overview of the Efficacy of Hormonal Replacement Therapy", *American Journal of Obstetrics and Gynecology*, May 1987 pp 1298-1303, Dr. Ettinger states that after ten years following reduced estrogen levels as a result of natural menopause or due to oophorectomy a women's trabecular bone loss is depleted enough that it may approach the fracture threshold. It is also stated that the fracture threshold for cortical bone is usually not reached until a women reaches her mid-seventies at which time hip fractures occur with fairly high frequency. In an article[3] by Dr. B. Lawrence Riggs entitled "Pathogenesis of Osteoporosis", *American Journal of Obstetrics and Gynecology*, May 1987 pp 1342–1346, it is stated that osteoporosis can be considered of two types, type one being a post-menopausal osteoporosis which occurs in women within fifteen to twenty years of the menopause and is related to acceleration of bone loss, and type 2 osteoporosis characterized by slow bone loss which is age related and begins at approximately age thirty and continues throughout the person's life. Type two osteoporosis is associated with both cortical and trabecular bone loss and fractures of this type occur primarily to the hip. Bone loss associated with type one osteoporosis primarily affects trabecular bone which leads typically to fractures of the vertebrae and ultra-distal radius, sites of large amounts of trabecular bone.

It has been experimentally found from a study which has been conducted by the applicant that a calendar-oriented regimen for post-menopausal women comprising the use of conjugated estrogen, medroxyprogesterone acetate and calcium carbonate is not only effective in treating certain post-menopausal symptoms, such as hot flushes and vaginal atrophy, but also gives rise to an increase in the patient's bone density for a substantial proportion of patients receiving the regimen. The unexpectedness of this finding is dramatic in view of the fact that such increase in bone density appears to occur in patients regardless of the age of the patient at the time the regimen is initiated, a finding which is at variance with the medical literature concerning the treatment of osteoporosis.

The particular regimen which is found to be efficacious in treating osteoporosis by stabilizing and in most cases increasing bone density comprises a calendar-oriented regimen as set forth in Table 1 below.

TABLE 1

| calendar days 1–25 | 0.625 mg conjugated estrogen |
| calendar days 16–25 | 10 mg medroxyprogesterone acetate |
| calendar days 26-end of month | 500 mg calcium carbonate |

Such a regimen in terms of estrogen, progesterone and calcium use is disclosed in U.S. Pat. No. 4,534,468 and with regard to the specific formulation and dosages in U.S. application Ser. No. 764,945, now U.S. Pat. No. 4,736,849, with respect to treating the symptoms of menopause. At the time of filing these applications, it was the belief of the present applicant that such a regimen would at best retard the effects of osteoporosis and would not increase bone density.

The dispenser 20 used in the present study is shown in FIGS. 1–4, corresponding to the dispenser disclosed in application Ser. No. 764,945, now U.S. Pat. No. 4,736,849. The dispenser is thus calendar-oriented and comprises a carrier 22 onto which are positioned a plurality of pill-containing enclosures 24.

The pill-containing enclosures have domes 31 preferably fabricated from a clear thermoplastic material forming part of an overall thermoplastic sheet 26.

The lower portion of each enclosure includes a rupturable zone 36 formed from a sheet-like material 38, such as a metallized foil sheet.

Figure 4:
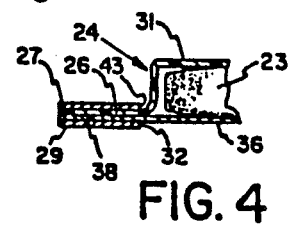
FIG. 4 is an enlarged view of the carrier and one pill-containing enclosure shown in FIG. 3 (the dotted circle) illustrating the upper and lower cardboard sheets forming the carrier, as well as the plastic sheet used to form the domes of the pill-containing enclosures and the metallized foil sheet used to form the rupturable zones for each such enclosure, the latter two sheets sandwiched between the cardboard sheets forming the carrier.

As seen in FIG. 4, plastic sheet 26 and foil sheet 38 are sandwiched between the carrier's front and rear cardboard sheets 27 and 28 with domes 31 passing through cutouts 43 in sheet 27.

Figure 2:
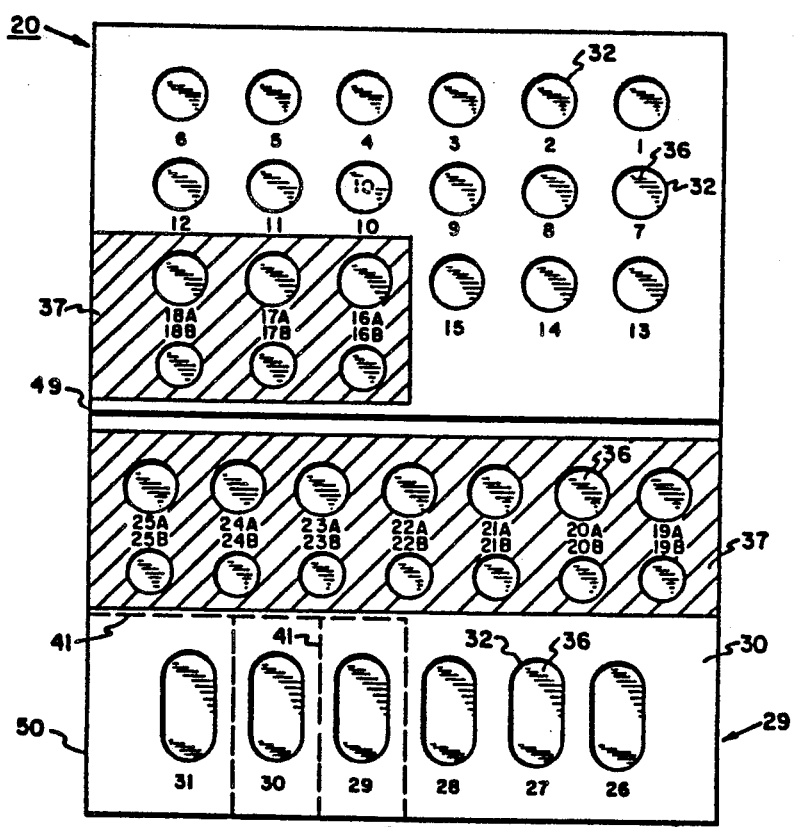
FIG. 2 is a bottom plan view of the dispenser shown in FIG. 1 showing the cutout portions on the rear surface of the carrier sheet which overlie the pill-containing enclosure rupturable zones formed by the foil sheet of the enclosures, and further showing that each cutout portion and corresponding zone have indicia associated therewith which correspond to the indicia shown on the front surface of the carrier corresponding to the calendar date for which the pill within the enclosure is to be taken.
Figure 1:
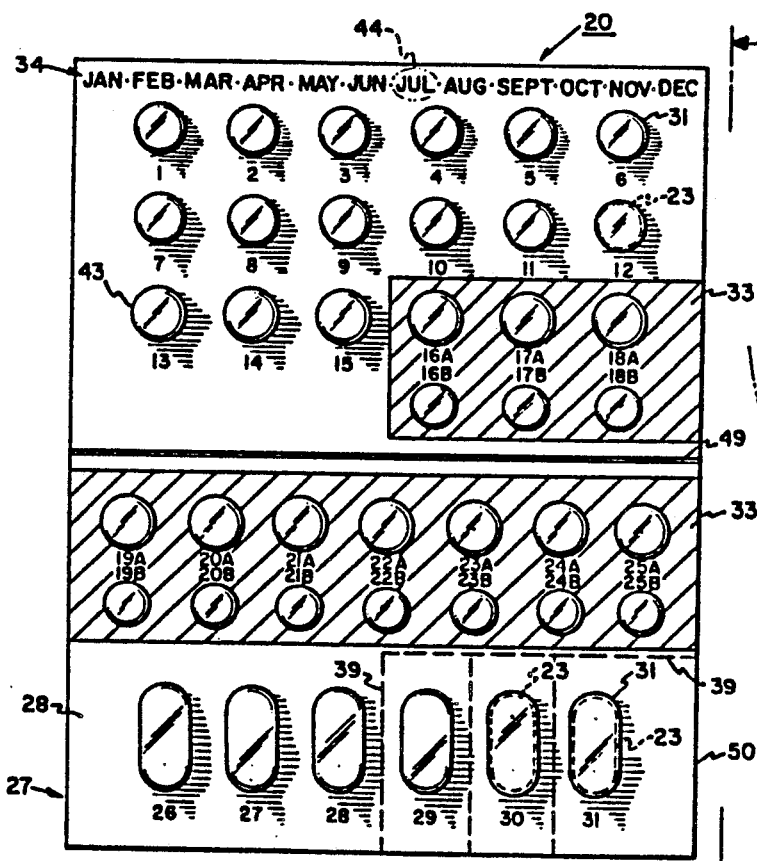
FIG. 1 is a top plan view of a dispenser for administering the calendar-oriented regimen according to the present invention so as to increase the bone density of post-menopausal women, the dispenser illustrating a carrier with a plurality of rows with pill-containing enclosures, each enclosure for the storage of a pill to be administered on a given calendar date and further showing numerical indicia for the calendar date positioned in proximity to the pill-containing enclosure whose pill is to be dispensed on a given calendar date.
Figure 3:
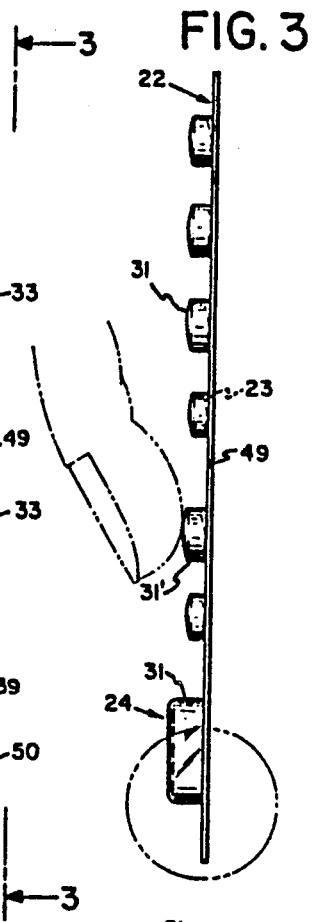
FIG. 3 is a side cross-sectional view taken along line 3—3 of FIG. 1 illustrating the manner in which the pill of each pill-containing enclosure is to be removed by rupturing the lower surface of the enclosure forming part of the backing sheet of the dispenser.

As seen in FIGS. 1 and 2, numerical indicia ranging from 1 to 31 identify each pill-containing enclosure on both the front and rear of the dispenser. Such indicia have been found to greatly enhance compliance with a calendar-oriented regimen.

The particular study conducted by the present applicant has comprised a group of seventy-nine post-menopausal women of which all but one showed low bone density, and thus an early sign of osteoporosis.

The test data for the sixty-four patients in this study who have had a follow-up bone density measurement is presented in Tables 2, 2A, 2B and 2C.

In this study, the patients have been tested using two bone density measuring techniques; namely, radiographic absorptiometry (RA) and dual photon absorptiometry (DPA).

TABLE 2

| PATIENT'S INITIALS | AGE AT 1ST DATE | 1ST DATE | DENS.[1] (AGE MATCHED) | 2ND DATE | DENS.[2] (AGE MATCHED) | DENS. CHANGE (AGE MATCHED) | REL. DENS. CHANGE (AGE MATCHED) | ELAPSED DAYS | RANK |
|---|---|---|---|---|---|---|---|---|---|
| JV | 55.0 | 01/03/85 | 98.7 | 12/08/86 | 105.7 | 7.0 | 7.00% | 704 | 1 |
| RD | 66.7 | 11/06/84 | 85.6 | 08/08/86 | 119.4 | 33.8 | 39.00% | 640 | 2 |
| DR | 65.0 | 06/07/85 | 70.4 | 09/18/86 | 121.3 | 50.9 | 72.00% | 468 | 3 |
| LG | 74.2 | 05/30/84 | 97.7 | 03/25/87 | 148.0 | 50.3 | 51.00% | 1029 | 4 |
| JB | 74.0 | 04/04/86 | 69.0 | 11/10/87 | 108.9 | 39.9 | 58.00% | 585 | 5 |
| JS | 53.9 | 11/19/85 | 65.0 | 07/02/87 | 85.4 | 20.4 | 31.00% | 590 | 6 |
| RW | 68.3 | 01/17/85 | 84.0 | 02/24/87 | 95.2 | 11.2 | 13.00% | 768 | 7 |
| MS | 75.2 | 10/29/84 | 85.5 | 08/13/87 | 129.8 | 44.3 | 52.00% | 1018 | 8 |
| AM | 73.1 | 11/25/85 | 82.0 | 06/15/87 | 115.6 | 33.6 | 41.00% | 567 | 9 |
| ED | 71.7 | 09/27/84 | 72.3 | 06/16/87 | 96.5 | 24.2 | 33.00% | 992 | 10 |
| NC | 46.6 | 10/17/84 | 86.0 | 06/10/87 | 89.2 | 3.2 | 4.00% | 966 | 11 |
| MD* | 71.68 | 04/26/84 | 91.5 | 06/09/87 | 111.4 | 19.9 | 22.00% | 1139 | 12 |
| AM** | 69.8 | 11/07/85 | 88.0 | 11/10/87 | 88.0 | 0.0 | 0.00% | 733 | 13 |
| EH** | 55.2 | 12/10/85 | 87.0 | 11/12/87 | 90.0 | 3.0 | 3.00% | 702 | 14 |
| AD** | 62.4 | 02/11/85 | 85.0 | 10/13/87 | 86.0 | 1.0 | 1.00% | 974 | 15 |
| MC** | 63.5 | 08/28/85 | 91.0 | 11/03/87 | 94.0 | 3.0 | 3.00% | 797 | 16 |
| PC**§ | 51.1 | 10/23/85 | 81.0 | 10/15/87 | 81.0 | | | 725 | 17 |
| BC**§§ | 64.8 | 08/13/85 | 82.0 | 11/12/87 | 80.0 | | | 821 | 18 |
| VB** | 63.7 | 10/24/84 | 96.0 | 11/17/87 | 98.0 | 2.0 | 2.00% | 1119 | 19 |
| RA** | 62.7 | 01/08/85 | 78.0 | 10/20/87 | 80.0 | 2.0 | 3.00% | 1015 | 20 |
| MB | 72.6 | 01/09/85 | 75.1 | 04/14/87 | 103.9 | 28.8 | 38.00% | 825 | 21 |
| BB | 76.3 | 07/31/84 | 62.2 | 10/21/87 | 99.7 | 37.5 | 60.00% | 1177 | 22 |
| EL | 65.2 | 04/17/85 | 87.1 | 08/11/86 | 99.6 | 12.5 | 14.00% | 846 | 23 |

TABLE 2-continued

| PATIENT'S INITIALS | AGE AT 1ST DATE | 1ST DATE | DENS.[1] (AGE MATCHED) | 2ND DATE | DENS.[2] (AGE MATCHED) | DENS. CHANGE (AGE MATCHED) | REL. DENS. CHANGE (AGE MATCHED) | ELAPSED DAYS | RANK |
|---|---|---|---|---|---|---|---|---|---|
| LB | 48.5 | 01/29/85 | 93.1 | 03/09/87 | 128.5 | 35.4 | 38.00% | 769 | 24 |
| AP | 60.0 | 01/10/85 | 84.0 | 03/10/87 | 120.4 | 36.4 | 43.00% | 789 | 25 |
| PR§§ | 46.7 | 12/10/85 | 101.0 | 08/12/86 | 85.1 | | | 245 | 26 |
| IS | 59.8 | 04/08/85 | 88.7 | 06/04/87 | 96.6 | 7.9 | 9.00% | 787 | 27 |
| IS | 60.0 | 10/18/84 | 69.0 | 03/24/87 | 106.9 | 37.9 | 55.00% | 887 | 28 |
| BV | 64.7 | 10/11/84 | 93.0 | 04/14/87 | 95.9 | 2.9 | 3.00% | 915 | 29 |
| MS | 55.3 | 03/07/85 | 76.8 | 10/23/87 | 89.6 | 12.8 | 17.00% | 960 | 30 |
| ID+ | 66.2 | 04/11/85 | 89.0 | 06/19/87 | 98.0 | 9.0 | 10.00% | 799 | 31 |
| CS | 73.1 | 03/27/85 | 85.8 | 03/25/87 | 91.9 | 6.1 | 7.00% | 728 | 32 |
| FK | 71.6 | 12/11/85 | 79.0 | 01/16/87 | 101.4 | 22.4 | 28.00% | 401 | 33 |
| GF | 60.0 | 01/18/85 | 113.2 | 04/29/87 | 128.1 | 14.9 | 13.00% | 831 | 34 |
| FF | 64.9 | 03/25/85 | 88.7 | 06/16/87 | 103.4 | 14.7 | 17.00% | 813 | 35 |
| DB** | 54.0 | 02/27/86 | 92.0 | 12/01/87 | 93.0 | 1.0 | 1.00% | 673 | 36 |
| CB** | 48 | 12/11/85 | 95.0 | 11/19/87 | 98.0 | 3.0 | 3.00% | 708 | 37 |
| HG** | 64 | 07/05/84 | 83.0 | 12/01/87 | 84.0 | 1.0 | 1.00% | 1244 | 38 |
| AJ**§§ | 69.9 | 02/13/85 | 77.0 | 12/01/87 | 76.0 | 1.0 | 1.00% | 1020 | 39 |
| DS** | 60.0 | 06/09/86 | 83.0 | 12/01/87 | 84.0 | 1.0 | 1.00% | 540 | 40 |
| TC** | 74.4 | 08/16/84 | 69.0 | 11/24/87 | 76.0 | 7.0 | 10.00% | 1195 | 41 |
| JG | 72.0 | 11/08/84 | 77.9 | 12/14/87 | 144.6 | 66.7 | 86.00% | 1131 | 42 |
| SG++ | 65.9 | 12/13/85 | 88.0 | 01/06/88 | 112.7 | 24.7 | 28.00% | 754 | 43 |
| TW | 66.8 | 07/03/84 | 106.1 | 02/09/88 | 130.3 | 24.2 | 23.00% | 1316 | 44 |
| EW | 90.3 | 10/29/84 | 73.0 | 02/11/88 | 87.9 | 14.9 | 20.00% | 835 | 45 |
| HA | 43.3 | 01/24/85 | 101.9 | 02/06/88 | 105.4 | 3.5 | 3.00% | 1108 | 46 |
| JC | 56.3 | 11/20/85 | 89.0 | 02/05/88 | 106.6 | 17.6 | 20.00% | 807 | 47 |
| EJ | 61.4 | 12/05/85 | 80.0 | 02/05/88 | 89.5 | 9.5 | 12.00% | 793 | 48 |
| DC | 54.3 | 02/19/85 | 96.2 | 02/06/88 | 116.0 | 20.4 | 21.00% | 1081 | 49 |
| MM | 52.2 | 10/18/84 | 101.0 | 02/09/88 | 116.6 | 15.0 | 15.00% | 1209 | 50 |
| MB*** | 74.0 | 02/05/87 | 96.5 | 01/22/88 | 104.4 | 7.9 | 8.20% | 351 | 51 |
| TA*** | 59 | 11/20/86 | 94.0 | 03/02/88 | 104.3 | 10.3 | 11.00% | 473 | 52 |
| EM | 58.8 | 08/24/84 | 102.7 | 03/01/88 | 110.3 | 7.6 | 7.40% | 1285 | 53 |
| CM*** | 39 | 04/06/87 | 82.9 | 02/22/88 | 85.7 | 2.8 | 3.40% | 320 | 54 |
| LP | 73.3 | 04/15/86 | 81.0 | 02/22/88 | 115.2 | 34.2 | 42.20% | 676 | 55 |
| NF | 61.8 | 12/19/85 | 95.0 | 03/08/88 | 132.2 | 37.2 | 39.16% | 810 | 56 |
| JC*** | 63.0 | 09/15/86 | 98.4 | 03/23/88 | 108.8 | 10.4 | 10.57% | 555 | 57 |
| AS | 67.1 | 11/05/85 | 89.0 | 03/23/88 | 107.5 | 18.5 | 20.79% | 869 | 58 |
| HN | 60.8 | 01/17/86 | 91.0 | 03/22/88 | 121.2 | 30.2 | 33.19% | 795 | 59 |
| EV*** | 74.0 | 08/06/86 | 72.4 | 03/19/88 | 76.6 | 4.2 | 5.80% | 591 | 60 |
| LP | 63.0 | 06/19/86 | 87.0 | 03/17/88 | 109.8 | 22.8 | 26.21% | 637 | 61 |
| JC*** | 30.0 | 11/06/86 | 90.4 | 03/24/88 | 95.0 | 4.6 | 5.09% | 504 | 62 |
| BM*** | 68.0 | 06/16/87 | 85.5 | 03/25/88 | 95.3 | 9.8 | 11.46% | 283 | 63 |
| AVERAGE | 63.2 | | 86.4 | | 104.0 | 17.6 | 21.35% | 804.69 | |

*Density #2 at Lumbar L2 (no L3 or L4 readings)
**Density #1 and Density #2 readings on radiographic absorptiometry
***Density #1 and Density #2 readings both on dual photon densitometer
+Density #2 at Lumbars L1-L3 (no L4 readings)
++Density #2 trachanteric
§Contraindicated (on cortesone treatment)
§§Did not comply with regimen
§§§Contraindicated (removed from regimen due to breast cancer)

TABLE 2A

Patient Data [11]
[W/W = Wedge 1st & 2nd Readings]
Rank Order & Average

| A | B | C | D | E | F | G | H | I | J | K |
|---|---|---|---|---|---|---|---|---|---|---|
| 1 | Pt | Age | 1st Date | Dens 1 | 2nd Date | Dens 2 | D/Ch 2-1 | Rel % Ch | Elap/T | Rank |
| 14 | AM | 69.8 | 11/07/85 | 88.0 | 11/10/87 | 88.0 | .0 | .00% | 733 | 13 |
| 15 | EH | 55.2 | 12/10/85 | 87.0 | 11/12/87 | 90.0 | 3.0 | 3.45% | 702 | 14 |
| 16 | AD | 62.4 | 02/11/85 | 85.0 | 10/13/87 | 86.0 | 1.0 | 1.18% | 974 | 15 |
| 17 | MC | 63.5 | 08/28/85 | 91.0 | 11/3/87 | 94.0 | 3.0 | 3.30% | 797 | 16 |
| 18 | VB | 63.7 | 10/24/84 | 96.0 | 11/17/87 | 98.0 | 2.0 | 2.08% | 1119 | 17 |
| 19 | #RA | 62.7 | 01/08/85 | 78.0 | 10/20/87 | 80.0 | 2.0 | 2.56% | 1015 | 18 |
| 34 | DB | 54.0 | 02/27/86 | 92.0 | 12/1/87 | 93.0 | 1.0 | 1.09% | 642 | 33 |
| 35 | CB | 48.5 | 12/11/85 | 95.0 | 11/19/87 | 98.0 | 3.0 | 3.16% | 708 | 34 |
| 36 | HG | 64.1 | 07/05/84 | 83.0 | 12/1/87 | 84.0 | 1.0 | 1.20% | 1244 | 35 |
| 37 | DS | 60.0 | 06/09/86 | 83.0 | 12/1/87 | 84.0 | 1.0 | 1.20% | 540 | 36 |
| 38 | TC | 74.4 | 08/16/84 | 69.0 | 11/24/87 | 76.0 | 7.0 | 10.14% | 1195 | 37 |
| Avg | | 61.7 | | 86.1 | | 88.3 | 2.2 | 2.67% | 879 | 61 |

TABLE 2B

DUAL PHOTON/DUAL PHOTON PATIENT DATA (7) RANK ORDER

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | RANK |
| 2 | 49 | MB | 74.0 | 2/5/87 | 96.5 | 1/22/88 | 104.4 | 7.9 | 8.19% | 351 | 48 |
| 3 | 50 | TA | 59.0 | 11/20/86 | 94.0 | 3/7/88 | 104.3 | 10.3 | 10.96% | 473 | 49 |
| 4 | 52 | CM | 39.0 | 4/6/87 | 82.9 | 2/20/88 | 85.7 | 2.8 | 3.38% | 320 | 51 |
| 5 | 55 | JC | 63.0 | 9/15/86 | 98.4 | 3/23/88 | 103.8 | 10.4 | 10.57% | 555 | 54 |
| 6 | 58 | EV | 74.0 | 8/6/86 | 72.4 | 3/19/88 | 76.6 | 4.2 | 5.80% | 591 | 57 |
| 7 | 60 | JC | 30.0 | 11/6/86 | 90.4 | 3/24/88 | 95.0 | 4.6 | 5.09% | 504 | 59 |
| 8 | 61 | BM | 68.0 | 6/16/87 | 85.5 | 3/25/88 | 95.3 | 9.8 | 11.46% | 283 | 60 |
| 9 | 62 | | 58.1 | | 88.6 | | 95.7 | 7.1 | 7.92% | 439.6 | 61 |

TABLE 2C

WEDGE/DUAL PHOTON PATIENT DATA (41) RANK ORDER

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | RANK |
| 2 | 2 | JV | 55.0 | 1/3/85 | 98.7 | 12/8/86 | 105.7 | 7.0 | 7.09% | 704 | 1 |
| 3 | 3 | RD | 66.7 | 11/6/84 | 85.6 | 8/8/86 | 119.4 | 33.8 | 39.49% | 640 | 2 |
| 4 | 4 | DR | 65.0 | 6/7/85 | 70.4 | 9/18/86 | 121.3 | 50.9 | 72.30% | 468 | 3 |
| 5 | 5 | LG | 74.2 | 5/30/84 | 97.7 | 3/25/87 | 148.0 | 50.3 | 51.48% | 1029 | 4 |
| 6 | 6 | JB | 74.0 | 4/4/86 | 69.0 | 11/10/87 | 108.9 | 39.9 | 57.83% | 585 | 5 |
| 7 | 7 | JS | 53.9 | 11/19/85 | 65.0 | 7/2/87 | 85.4 | 20.4 | 31.38% | 590 | 6 |
| 8 | 8 | RW | 68.3 | 1/17/85 | 84.0 | 2/24/87 | 95.2 | 11.2 | 13.33% | 768 | 7 |
| 9 | 9 | MS | 75.2 | 10/29/84 | 85.5 | 8/13/87 | 129.8 | 44.3 | 51.81% | 1018 | 8 |
| 10 | 10 | AM | 73.1 | 11/25/85 | 82.0 | 6/15/87 | 115.6 | 33.6 | 40.98% | 567 | 9 |
| 11 | 11 | ED | 71.7 | 9/27/84 | 72.3 | 6/16/87 | 96.5 | 24.2 | 33.47% | 992 | 10 |
| 12 | 12 | NC | 46.6 | 10/17/84 | 86.0 | 6/10/87 | 89.2 | 3.2 | 3.72% | 966 | 11 |
| 13 | 13 | MD | 71.8 | 4/26/84 | 91.5 | 6/9/87 | 111.4 | 19.9 | 21.75% | 1139 | 12 |
| 14 | 20 | MB | 72.6 | 1/9/85 | 75.1 | 4/14/87 | 103.9 | 28.8 | 38.35% | 825 | 19 |
| 15 | 21 | BB | 76.3 | 7/31/84 | 62.2 | 10/21/87 | 99.7 | 37.5 | 60.29% | 1177 | 20 |
| 16 | 22 | EL | 65.2 | 4/17/85 | 87.1 | 8/11/86 | 99.6 | 12.5 | 14.35% | 481 | 21 |
| 17 | 23 | LP | 48.5 | 1/29/85 | 93.1 | 3/9/87 | 128.5 | 35.4 | 38.02% | 769 | 22 |
| 18 | 24 | AP | 60.0 | 1/10/85 | 84.0 | 3/10/87 | 120.4 | 36.4 | 43.33% | 789 | 23 |
| 19 | 25 | IS | 59.8 | 4/8/85 | 88.7 | 6/4/87 | 96.6 | 7.9 | 8.91% | 787 | 24 |
| 20 | 26 | #IS | 60.0 | 10/18/84 | 69.0 | 3/24/87 | 106.9 | 37.9 | 54.93% | 887 | 25 |
| 21 | 27 | VB | 64.7 | 10/11/84 | 93.0 | 4/14/87 | 95.9 | 2.9 | 3.12% | 915 | 26 |
| 22 | 28 | MS | 55.3 | 3/7/85 | 76.8 | 10/23/87 | 89.6 | 12.8 | 16.67% | 960 | 27 |
| 23 | 29 | ID | 66.2 | 4/11/85 | 89.0 | 6/19/87 | 98.0 | 9.0 | 10.11% | 799 | 28 |
| 24 | 30 | CS | 73.1 | 3/27/85 | 85.8 | 3/25/87 | 91.9 | 6.1 | 7.11% | 728 | 29 |
| 25 | 31 | FK | 71.6 | 12/11/85 | 79.0 | 1/16/87 | 101.4 | 22.4 | 28.35% | 401 | 30 |
| 26 | 32 | GF | 60.0 | 1/18/85 | 113.2 | 4/29/87 | 128.1 | 14.9 | 13.16% | 831 | 31 |
| 27 | 33 | FF | 64.9 | 3/25/85 | 88.7 | 6/16/87 | 103.5 | 14.8 | 16.69% | 813 | 32 |
| 28 | 39 | JG | 72.0 | 11/8/84 | 77.9 | 12/14/87 | 144.6 | 66.7 | 85.62% | 1131 | 38 |
| 29 | 40 | SG | 65.9 | 12/13/85 | 88.0 | 1/6/88 | 112.7 | 24.7 | 28.07% | 754 | 39 |
| 30 | 41 | TW | 66.8 | 7/3/84 | 106.1 | 2/9/88 | 130.3 | 24.2 | 22.81% | 1316 | 40 |
| 31 | 42 | EW | 90.3 | 10/29/85 | 73.0 | 2/11/88 | 87.9 | 14.9 | 20.41% | 835 | 41 |
| 32 | 43 | HA | 43.3 | 1/24/85 | 101.9 | 2/6/88 | 105.4 | 3.5 | 3.43% | 1108 | 42 |
| 33 | 44 | JC | 56.3 | 11/20/85 | 89.0 | 2/5/88 | 106.6 | 17.6 | 19.78% | 807 | 43 |
| 34 | 45 | EJ | 61.4 | 12/5/85 | 80.0 | 2/5/88 | 89.5 | 9.5 | 11.88% | 792 | 44 |
| 35 | 46 | DC | 54.3 | 2/19/85 | 96.2 | 2/5/88 | 116.0 | 19.8 | 20.58% | 1081 | 45 |
| 36 | 47 | MM | 52.2 | 10/18/84 | 101.0 | 2/9/88 | 116.6 | 15.6 | 15.45% | 1209 | 46 |
| 37 | 51 | EM | 58.8 | 8/24/84 | 102.7 | 3/1/88 | 110.3 | 7.6 | 7.40% | 1285 | 50 |
| 38 | 53 | LP | 73.3 | 4/15/86 | 81.0 | 2/20/88 | 115.2 | 34.2 | 42.22% | 676 | 52 |
| 39 | 54 | NF | 61.8 | 12/19/85 | 95.0 | 3/8/88 | 132.2 | 37.2 | 39.16% | 810 | 53 |
| 40 | 56 | AS | 67.1 | 11/5/85 | 89.0 | 3/23/88 | 107.5 | 18.5 | 20.79% | 869 | 55 |
| 41 | 57 | HN | 60.8 | 1/17/86 | 91.0 | 3/22/88 | 121.2 | 30.2 | 33.19% | 795 | 56 |
| 42 | 59 | LP | 63.0 | 6/19/86 | 87.0 | 3/17/88 | 109.8 | 22.8 | 26.21% | 637 | 58 |
| 43 | 62 | | 64.4 | | 86.1 | | 109.7 | 23.5 | 28.66% | 847.1 | 61 |

The radiographic absorptiometry (RA) measurements were made by Clinical Radiology Testing Laboratory, Box 478, Yellow Springs, Ohio 45387, based upon radiographs of the patient's middle phalanges taken at the Melrose-Wakefield Hospital in Melrose, Mass. The radiographs were taken with an aluminum step "wedge" of known densities in the field of view for calibrating the density measurements made by the Clinical Radiology Testing Laboratory. The dual photon absorptiometry (DPA) measurements were made at the Melrose-Wakefield Hospital in Melrose, Mass. using a Lunar Radiation Corporation (916 Williamson Street, Madison, WI, 53703) model densitometer DP #3 spine-femur scanner, employing a gadolinium-153 source with the predominant energies of 44 and 120 kev (thousand electron volt). These measurements were made of the lumbar vertebrae (typically L2-L4) except for patient SG.

The patients listed without special symbols next to their initials were first tested by radiographic absorptiometry and later tested by dual-photon absorptiometry. The patients having a double asterisk () next to their initials were tested on both occasions by radiographic absorpitometry while those patients having a triple asterisk (*) next to their initials were tested on both occasions by a dual photon absorptiometry.

According to published reports [13,14] the radiographic absorptiometry measurement process has accuracy (ability to correctly determine a parameter) of 5 to 15 percent and precision (repeatability from reading to reading, independent of accuracy) of 1.5 to 5 percent range. However, according to personnel at Clinical Radiology Testing Laboratory, their accuracy and precision are approximately 3 percent and 2 percent respectively. It is reported however, that RA measurements do not correlate well with bone density in other skeletal locations, such as the axial skeleton.[14] FIG. 5 shows the output of a typical radiographic absorptiometry measurement (patient JV). This data plots the measured bone mineral density for the patient's age against the bone mineral density for normal women in the age bracket of twenty to fifty years. The bone mineral density has a value related to the relative mass of the bone per unit area. The mean mineral density is thus the mean for normal women between the ages of twenty to fifty years while the −1SD and +1SD correspond to minus one and plus one standard deviation for such women.

For the example shown in FIG. 5 corresponding to patient JV in Table 2, the woman's bone mineral density on 3 Jan. 1985 was 98.7 which is −1.11 standard deviations less than normal women between the ages of twenty to fifty.

Dual photon absorptiometry measurements have good accuracy (4 percent to 10 percent in vivo) and precision (0.7 percent to 6 percent).[15] The results from this measurement process are expressed in grams per square centimeter, which is often referred to as bone mineral density (BMD). These measurements can also be adjusted for the patient's sex, age, ethnic background and weight so as to yield an age adjusted measurement which indicates the patient's bone density in comparison to others of similar background and age. FIG. 6 shows the output for patient JV using the dual photon bone density measurement process. This woman's L2 to L4 vertebrae bone mineral content is 1.128 gm/cm$^2$, which when age matched for a woman of fifty-seven years of age is 105.7 percent of the mean value for such women (her bone density for L2 to L4 is in the upper normal range).

Although the RA measurements are made using the patient's middle phalanges while the dual photon measurements are made using the patient's vertebrae, the bone density measurements are believed to have positive correlation in view of the findings discernible from those patients where both measurements were made at the same skeletal site using the same measuring technique (see Table 2A for patients having only RA measurements and Table 2B for patients having only DPA measurements as compared to Table 2C for patients where the first measurement was made by RA and the second measurement was made by DPA). Such correlations are believed to be more favorable than those determined by Reinbold et al[14] for spinal and appendicular cortical measurements. The correlation of the present data is comparable to that found in the Ott et al article.[16]

Consequently, it is believed that the test data can be compared for the patients whether such data for the patients is based on RA-RA, RA-DPA, or DPA-DPA measurements. It is therefore believed that statistical analysis of this data is appropriate.

This test data shows that with the exception of individuals who were on other medications which contraindicated continuation of the regimen (such as use of cortisone) or who were not compliant in the usage of the regimen, the patients all show improvement in bone density, or no decrease in bone density. As seen at the last line of Table 2, the average age matched bone density increase for the patients is 21.35 percent. This average is based upon all patients who were compliant with the regimen and who were not contraindicated due to administration of other medication. The average bone increases for Tables 2A, 2B and 2C are 2.67 percent, 7.92 percent and 28.66% respectively.

Although the average bone increase for patients when both measurements were taken with RA (see Table 2A, last row) is substantially less than those when both measurements were taken with DPA (see Table 2B, last row), this result in part at least is believed to be due to the higher percentage of cortical bone in the phalanges as compared to the spine. The present invention is believed to act predominately on trabecular bone.

It is also apparent that although the patients for whom the first measurements were taken with DPA have an average increase in bone density (see Table 2C, last row) substantially higher than Table 2A or Table 2B patients, this result is believed to be at least in part due to the higher trabecular bone content of the spine used in the second measurements.

Table 3 is a rearrangement of the data presented in Table 2 in patient age ascending order. FIG. 7 is a graphical representation of this data and FIG. 8 is a graphical representation of this data averaged by patient age using linear regression analysis. It is apparent from FIG. 8 that the absolute change in density per patient (which typically comprised approximately a two year time span) has a slight positive correlation to age; that is, the change in density is relatively independent of the age at which the patient initiated the regimen, and indeed may show slightly greater improvement as the patient's starting age increases. This result indicates that this therapy is effective even though initiated many years after the onset of menopause and consequently the regimen could potentially correct or reduce the severity of osteoporosis even for women of relatively advanced years. Such a result is directly contrary to the prevailing medical literature.

TABLE 3

| | | Pt | Age | 1st Date | Dens 1 | Patient Data [59] AGE 2nd Date | Dens 2 | D/Ch 2-1 | Rel % Ch | Elap/T | Rank |
|---|---|---|---|---|---|---|---|---|---|---|---|
| 1 | 1 | | | | | | | | | | |
| 2 | 60 | JC | 30.0 | 11/06/86 | 90.4 | 3/24/88 | 95.0 | 4.6 | 5.09% | 504 | 59 |
| 3 | 52 | CM | 39.0 | 04/06/87 | 82.9 | 2/20/88 | 85.7 | 2.8 | 3.38% | 320 | 51 |
| 4 | 43 | HA | 43.3 | 01/24/85 | 101.9 | 2/6/88 | 105.4 | 3.5 | 3.43% | 1108 | 42 |
| 5 | 12 | NC | 46.6 | 10/17/84 | 86.0 | 6/10/87 | 89.2 | 3.2 | 3.72% | 966 | 11 |
| 6 | 23 | LP | 48.5 | 01/29/85 | 93.1 | 3/9/87 | 128.5 | 35.4 | 38.02% | 769 | 22 |
| 7 | 35 | CB | 48.5 | 12/11/85 | 95.0 | 11/19/87 | 98.0 | 3.0 | 3.16% | 708 | 34 |
| 8 | 47 | MM | 52.2 | 10/18/84 | 101.0 | 2/9/88 | 116.6 | 15.6 | 15.45% | 1209 | 46 |

TABLE 3-continued

Patient Data [59]  
AGE

| 1 | 1 Pt | Age | 1st Date | Dens 1 | 2nd Date | Dens 2 | D/Ch 2-1 | Rel % Ch | Elap/T | Rank |
|---|------|-----|----------|--------|----------|--------|----------|----------|--------|------|
| 9 | 7 JS | 53.9 | 11/19/85 | 65.0 | 7/2/87 | 85.4 | 20.4 | 31.38% | 590 | 6 |
| 10 | 34 DB | 54.0 | 02/27/86 | 92.0 | 12/1/87 | 93.0 | 1.0 | 1.09% | 642 | 33 |
| 11 | 46 DC | 54.3 | 02/19/85 | 96.2 | 2/5/88 | 116.0 | 19.8 | 20.58% | 1081 | 45 |
| 12 | 2 JV | 55.0 | 01/03/85 | 98.7 | 12/8/86 | 105.7 | 7.0 | 7.09% | 704 | 1 |
| 13 | 15 EH | 55.2 | 12/10/85 | 87.0 | 11/12/87 | 90.0 | 3.0 | 3.45% | 702 | 14 |
| 14 | 28 MS | 55.3 | 03/07/85 | 76.8 | 10/23/87 | 89.6 | 12.8 | 16.67% | 960 | 27 |
| 15 | 44 JC | 56.3 | 11/20/85 | 89.0 | 2/5/88 | 106.6 | 17.6 | 19.78% | 807 | 43 |
| 16 | 51 EM | 58.8 | 08/24/84 | 102.7 | 3/1/88 | 110.3 | 7.6 | 7.40% | 1285 | 50 |
| 17 | 50 TA | 59.0 | 11/20/86 | 94.0 | 3/7/88 | 104.3 | 10.3 | 10.96% | 473 | 49 |
| 18 | 25 IS | 59.8 | 04/08/85 | 88.7 | 6/4/87 | 96.6 | 7.9 | 8.91% | 787 | 24 |
| 19 | 24 AP | 60.0 | 01/10/85 | 84.0 | 3/10/87 | 120.4 | 36.4 | 43.33% | 789 | 23 |
| 20 | 26 #IS | 60.0 | 10/18/84 | 69.0 | 3/24/87 | 106.9 | 37.9 | 54.93% | 887 | 25 |
| 21 | 32 GF | 60.0 | 01/18/85 | 113.2 | 4/29/87 | 128.1 | 14.9 | 13.16% | 831 | 31 |
| 22 | 37 DS | 60.0 | 06/09/86 | 83.0 | 12/1/87 | 84.0 | 1.0 | 1.20% | 540 | 36 |
| 23 | 57 HN | 60.8 | 01/17/86 | 91.0 | 3/22/88 | 121.2 | 30.2 | 33.19% | 795 | 56 |
| 24 | 45 EJ | 61.4 | 12/05/85 | 80.0 | 2/5/88 | 89.5 | 9.5 | 11.88% | 792 | 44 |
| 25 | 54 NF | 61.8 | 12/19/85 | 95.0 | 3/8/88 | 132.2 | 37.2 | 39.16% | 810 | 53 |
| 26 | 16 AD | 62.4 | 02/11/85 | 85.0 | 10/13/87 | 86.0 | 1.0 | 1.18% | 974 | 15 |
| 27 | 19 #RA | 62.7 | 01/08/85 | 78.0 | 10/20/87 | 80.0 | 2.0 | 2.56% | 1015 | 18 |
| 28 | 55 JC | 63.0 | 09/15/86 | 98.4 | 3/23/88 | 108.8 | 10.4 | 10.57% | 555 | 54 |
| 29 | 59 LP | 63.0 | 06/19/86 | 87.0 | 3/17/88 | 109.8 | 22.8 | 26.21% | 637 | 58 |
| 30 | 17 MC | 63.5 | 08/28/85 | 91.0 | 11/3/87 | 94.0 | 3.0 | 3.30% | 797 | 16 |
| 31 | 18 VB | 63.7 | 10/24/84 | 96.0 | 11/17/87 | 98.0 | 2.0 | 2.08% | 1119 | 17 |
| 32 | 36 HG | 64.1 | 07/05/84 | 83.0 | 12/1/87 | 84.0 | 1.0 | 1.20% | 1244 | 35 |
| 33 | 27 VB | 64.7 | 10/11/84 | 93.0 | 4/14/87 | 95.9 | 2.9 | 3.12% | 915 | 26 |
| 34 | 33 FF | 64.9 | 03/25/85 | 88.7 | 6/16/87 | 103.5 | 14.8 | 16.69% | 813 | 32 |
| 35 | 4 DR | 65.0 | 06/07/85 | 70.4 | 9/18/86 | 121.3 | 40.9 | 72.30% | 468 | 3 |
| 36 | 22 EL | 65.2 | 04/17/85 | 87.1 | 8/11/86 | 99.6 | 12.5 | 14.35% | 481 | 21 |
| 37 | 40 SG | 65.9 | 12/13/85 | 88.0 | 1/6/88 | 112.7 | 24.7 | 28.07% | 754 | 39 |
| 38 | 29 ID | 66.2 | 04/11/85 | 89.0 | 6/19/87 | 98.0 | 9.0 | 10.11% | 799 | 28 |
| 39 | 3 RD | 66.7 | 11/06/84 | 85.6 | 8/8/86 | 119.4 | 33.8 | 39.49% | 640 | 2 |
| 40 | 41 TW | 66.8 | 07/03/84 | 106.1 | 2/9/88 | 130.3 | 24.2 | 22.81% | 1316 | 40 |
| 41 | 56 AS | 67.1 | 11/05/85 | 89.0 | 3/23/88 | 107.5 | 18.5 | 20.79% | 869 | 55 |
| 42 | 61 BM | 68.0 | 06/18/87 | 85.5 | 3/25/88 | 95.3 | 9.8 | 11.46% | 281 | 60 |
| 43 | 8 RW | 68.3 | 01/17/85 | 84.0 | 2/24/87 | 95.2 | 11.2 | 13.33% | 768 | 7 |
| 44 | 14 AM | 69.8 | 11/07/85 | 88.0 | 11/10/87 | 88.0 | .0 | .00% | 733 | 13 |
| 45 | 31 FK | 71.6 | 12/11/85 | 79.0 | 1/16/87 | 101.4 | 22.4 | 28.35% | 401 | 30 |
| 46 | 11 ED | 71.7 | 09/27/84 | 72.3 | 6/16/87 | 96.5 | 24.2 | 33.47% | 992 | 10 |
| 47 | 13 MD | 71.8 | 04/26/84 | 91.5 | 6/9/87 | 111.4 | 19.9 | 21.75% | 1139 | 12 |
| 48 | 39 JG | 72.0 | 11/08/84 | 77.9 | 12/14/87 | 144.6 | 66.7 | 85.62% | 1131 | 38 |
| 49 | 20 MB | 72.6 | 01/09/85 | 75.1 | 4/14/87 | 103.9 | 28.8 | 38.35% | 825 | 19 |
| 50 | 10 AM | 73.1 | 11/25/85 | 82.0 | 6/15/87 | 115.6 | 33.6 | 40.98% | 567 | 9 |
| 51 | 30 CS | 73.1 | 03/27/85 | 85.8 | 3/25/87 | 91.9 | 6.1 | 7.11% | 728 | 29 |
| 52 | 53 LP | 73.3 | 04/15/86 | 81.0 | 2/20/88 | 115.2 | 34.2 | 42.22% | 676 | 52 |
| 53 | 6 JB | 74.0 | 04/04/86 | 69.0 | 11/10/87 | 108.9 | 39.9 | 57.83% | 585 | 5 |
| 54 | 49 MB | 74.0 | 02/05/87 | 96.5 | 1/22/88 | 104.4 | 7.9 | 8.19% | 351 | 48 |
| 55 | 58 EV | 74.0 | 08/06/86 | 72.4 | 3/19/88 | 76.6 | 4.2 | 5.80% | 591 | 57 |
| 56 | 5 LG | 74.2 | 05/30/84 | 97.7 | 3/25/87 | 148.0 | 50.3 | 51.48% | 1029 | 4 |
| 57 | 38 TC | 74.4 | 08/16/84 | 69.0 | 11/24/87 | 76.0 | 7.0 | 10.14% | 1195 | 37 |
| 58 | 9 MS | 75.2 | 10/29/84 | 85.5 | 8/13/87 | 129.8 | 44.3 | 51.81% | 1018 | 8 |
| 59 | 21 BB | 76.3 | 07/31/84 | 62.2 | 10/21/87 | 99.7 | 37.5 | 60.29% | 1177 | 20 |
| 60 | 42 EW | 90.3 | 10/29/85 | 73.0 | 2/11/88 | 87.9 | 14.9 | 20.41% | 835 | 41 |
| Ave | | 63.2 | | 86.4 | | 104.0 | 17.6 | 21.35 | 804.7 | |

TABLE 3A

Patient Data [11]  
AGE

| A | B | C | D | E | F | G | H | I | J | K |
|---|---|---|---|---|---|---|---|---|---|---|
| 1 | Pt | Age | 1st Date | Dens 1 | 2nd Date | Dens 2 | D/Ch 2-1 | Rel % Ch | Elap/T | Rank |
| 35 | CB | 48.5 | 12/11/85 | 95.0 | 11/19/87 | 98.0 | 3.0 | 3.16% | 708 | 34 |
| 34 | DB | 54.0 | 02/27/86 | 92.0 | 12/1/87 | 93.0 | 1.0 | 1.09% | 642 | 33 |
| 15 | EH | 55.2 | 12/10/85 | 87.0 | 11/12/87 | 90.0 | 3.0 | 3.45% | 702 | 14 |
| 37 | DS | 60.0 | 06/09/86 | 83.0 | 12/1/87 | 84.0 | 1.0 | 1.20% | 540 | 36 |
| 16 | AD | 62.4 | 02/11/85 | 85.0 | 10/13/87 | 86.0 | 1.0 | 1.18% | 974 | 15 |
| 19 | #RA | 62.7 | 01/08/85 | 78.0 | 10/20/87 | 80.0 | 2.0 | 2.56% | 1015 | 18 |
| 17 | MC | 63.5 | 08/28/85 | 91.0 | 11/3/87 | 94.0 | 3.0 | 3.30% | 797 | 16 |
| 18 | VB | 63.7 | 10/24/84 | 96.0 | 11/17/87 | 98.0 | 2.0 | 2.08% | 1119 | 17 |
| 36 | HG | 64.1 | 07/05/84 | 83.0 | 12/1/87 | 84.0 | 1.0 | 1.20% | 1244 | 35 |
| 14 | AM | 69.8 | 11/07/85 | 88.0 | 11/10/87 | 88.0 | .0 | .00% | 733 | 13 |
| 38 | TC | 74.4 | 08/16/84 | 69.0 | 11/24/87 | 76.0 | 7.0 | 10.14% | 1195 | 37 |
| Ave | | 61.7 | | 86.1 | | 88.3 | 2.2 | 2.67% | 879 | 61 |

TABLE 3B

DUAL PHOTON/DUAL PHOTON PATIENT DATA (7)

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | RANK |
| 2 | 60 | JC | 30.0 | 11/6/86 | 90.4 | 3/24/88 | 95.0 | 4.6 | 5.09% | 504 | 59 |
| 3 | 52 | CM | 39.0 | 4/6/87 | 82.9 | 2/20/88 | 85.7 | 2.8 | 3.38% | 320 | 51 |
| 4 | 50 | TA | 59.0 | 11/20/86 | 94.0 | 3/7/88 | 104.3 | 10.3 | 10.96% | 473 | 49 |
| 5 | 55 | JC | 63.0 | 9/15/86 | 98.4 | 3/23/88 | 108.8 | 10.4 | 10.57% | 555 | 54 |
| 6 | 61 | BM | 68.0 | 6/16/87 | 85.5 | 3/25/88 | 95.3 | 9.9 | 11.46% | 283 | 60 |
| 7 | 49 | MB | 74.0 | 2/5/87 | 96.5 | 1/22/88 | 104.4 | 7.9 | 8.19% | 351 | 48 |
| 8 | 58 | EV | 74.0 | 8/6/86 | 72.4 | 3/19/88 | 76.6 | 4.2 | 5.80% | 591 | 57 |

TABLE 3C

WEDGE/DUAL PHOTON PATIENT DATA (41)

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | RANK |
| 2 | 43 | HA | 43.3 | 1/24/85 | 101.9 | 2/6/88 | 105.4 | 3.5 | 3.43% | 1108 | 42 |
| 3 | 12 | NC | 46.6 | 10/17/84 | 86.0 | 6/10/87 | 89.2 | 3.2 | 3.72% | 956 | 11 |
| 4 | 23 | LP | 48.5 | 1/29/85 | 93.1 | 3/9/87 | 128.5 | 35.4 | 38.02% | 769 | 22 |
| 5 | 47 | MM | 52.2 | 10/18/84 | 101.0 | 2/9/88 | 116.6 | 15.6 | 15.45% | 1209 | 46 |
| 6 | 7 | JS | 53.9 | 11/19/85 | 65.0 | 7/2/87 | 85.4 | 20.4 | 31.38% | 590 | 6 |
| 7 | 46 | DC | 54.3 | 2/19/85 | 96.2 | 2/5/88 | 116.0 | 19.8 | 20.58% | 1081 | 45 |
| 8 | 2 | JV | 55.0 | 1/3/85 | 98.7 | 12/8/86 | 105.7 | 7.0 | 7.09% | 704 | 1 |
| 9 | 28 | MS | 55.3 | 3/7/85 | 76.8 | 10/23/87 | 89.6 | 12.8 | 16.67% | 960 | 27 |
| 10 | 44 | JC | 56.3 | 11/20/85 | 89.0 | 2/5/88 | 106.6 | 17.6 | 19.78% | 507 | 43 |
| 11 | 51 | EM | 58.8 | 8/24/84 | 102.7 | 3/1/88 | 110.3 | 7.6 | 7.40% | 1285 | 50 |
| 12 | 25 | IS | 59.8 | 4/8/85 | 88.7 | 6/4/87 | 96.6 | 7.9 | 8.91% | 787 | 24 |
| 13 | 24 | AP | 60.0 | 1/10/85 | 84.0 | 3/10/87 | 120.4 | 36.4 | 43.33% | 789 | 23 |
| 14 | 26 | #IS | 60.0 | 10/18/84 | 69.0 | 3/24/87 | 106.9 | 37.9 | 54.93% | 887 | 25 |
| 15 | 32 | GF | 60.0 | 1/18/85 | 113.2 | 4/29/87 | 128.1 | 14.9 | 13.16% | 831 | 31 |
| 16 | 57 | HN | 60.8 | 1/17/86 | 91.0 | 3/22/88 | 121.2 | 30.2 | 33.19% | 795 | 56 |
| 17 | 45 | EJ | 61.4 | 12/5/85 | 80.0 | 2/5/88 | 89.5 | 9.5 | 11.88% | 792 | 44 |
| 18 | 54 | NF | 61.8 | 12/19/85 | 95.0 | 3/8/88 | 132.2 | 37.2 | 39.16% | 810 | 53 |
| 19 | 59 | LP | 63.0 | 6/19/86 | 87.0 | 3/17/88 | 109.8 | 22.8 | 26.21% | 637 | 58 |
| 20 | 27 | VB | 64.7 | 10/11/84 | 93.0 | 4/14/87 | 95.9 | 2.9 | 3.12% | 915 | 26 |
| 21 | 33 | FF | 64.9 | 3/25/85 | 88.7 | 6/16/87 | 103.5 | 14.8 | 16.69% | 813 | 32 |
| 22 | 4 | DR | 65.0 | 6/7/85 | 70.4 | 9/18/86 | 121.3 | 50.9 | 72.30% | 468 | 3 |
| 23 | 22 | EL | 65.2 | 4/17/85 | 87.1 | 8/11/86 | 99.6 | 12.5 | 14.35% | 481 | 21 |
| 24 | 40 | SG | 65.9 | 12/13/85 | 88.0 | 1/6/88 | 112.7 | 24.7 | 28.07% | 754 | 39 |
| 25 | 29 | ID | 66.2 | 4/11/85 | 89.0 | 6/19/87 | 98.0 | 9.0 | 10.11% | 799 | 28 |
| 26 | 3 | RD | 66.7 | 11/6/84 | 85.6 | 8/8/86 | 119.4 | 33.8 | 39.49% | 640 | 2 |
| 27 | 41 | TW | 66.8 | 7/3/84 | 106.1 | 2/9/88 | 130.3 | 24.2 | 22.81% | 1316 | 40 |
| 28 | 56 | AS | 67.1 | 11/5/85 | 89.0 | 3/23/88 | 107.5 | 18.5 | 20.79% | 869 | 55 |
| 29 | 8 | RW | 68.3 | 1/17/85 | 84.0 | 2/24/87 | 95.2 | 11.2 | 13.33% | 768 | 7 |
| 30 | 31 | FK | 71.6 | 12/11/85 | 79.0 | 1/16/87 | 101.4 | 22.4 | 28.35% | 401 | 30 |
| 31 | 11 | ED | 71.7 | 9/27/84 | 72.3 | 6/16/87 | 96.5 | 24.2 | 33.47% | 992 | 10 |
| 32 | 13 | MD | 71.8 | 4/26/84 | 91.5 | 6/9/87 | 111.4 | 19.9 | 21.75% | 1139 | 12 |
| 33 | 39 | JG | 72.0 | 11/8/84 | 77.9 | 12/14/87 | 144.6 | 66.7 | 85.62% | 1131 | 38 |
| 34 | 20 | MB | 72.6 | 1/9/85 | 75.1 | 4/14/87 | 103.9 | 28.8 | 38.35% | 825 | 19 |
| 35 | 10 | AM | 73.1 | 11/25/85 | 82.0 | 6/15/87 | 115.6 | 33.6 | 40.98% | 567 | 9 |
| 36 | 30 | CS | 73.1 | 3/27/85 | 85.8 | 3/25/87 | 91.9 | 6.1 | 7.11% | 728 | 29 |
| 37 | 53 | LP | 73.3 | 4/15/86 | 81.0 | 2/20/88 | 115.2 | 34.2 | 42.22% | 676 | 52 |
| 38 | 6 | JB | 74.0 | 4/4/86 | 69.0 | 11/10/87 | 108.9 | 39.9 | 57.83% | 585 | 5 |
| 39 | 5 | LG | 74.2 | 5/30/84 | 97.7 | 3/25/87 | 148.0 | 50.3 | 51.48% | 1029 | 4 |
| 40 | 9 | MS | 75.2 | 10/29/84 | 85.5 | 8/13/87 | 129.8 | 44.3 | 51.81% | 1018 | 8 |
| 41 | 21 | BB | 76.3 | 7/31/84 | 62.2 | 10/21/87 | 99.7 | 37.5 | 60.29% | 1177 | 20 |
| 42 | 42 | EW | 90.3 | 10/29/85 | 73.0 | 2/11/88 | 87.9 | 14.9 | 20.41% | 835 | 41 |

Table 3A, 3B and 3C are respective rearrangements of the data presented in Tables 2A, 2B and 2C in patient age ascending order. FIGS. 7A, 7B and 7C are respective graphical representations of the data presented in Tables 3A, 3B and 3C while FIG. 8A, 8B and 8C are graphical representations of this data averaged by patient age using linear regression analysis.

It is apparent that all subgroups of patients show an average increase in bone density (see Tables 2A, 2B and 2C), while FIGS. 8A-8C show a positive correlation between bone density improvement and age. Such a result is directly contrary to the prevailing medical literature which states that bone improvement, if possible at all, is seen only if estrogen is taken shortly after menopause.

FIG. 9, corresponding to Table 4, is a rearrangement of the data in Table 2 based upon the length of time the women have been on the regimen FIG. 10 is a linear regression analysis of the data shown in FIG. 9 and shows a small positive correlation between the length of time on the regimen and the amount of bone density increase.

Table 5 sorts the data from Table 2 so as to show the change in patient density as it relates to the starting density of the patient. FIG. 11 is a plot of this data arrangement while FIG. 12 is a linear regression analysis between change in density and the patient's starting density. FIG. 12 shows that the change in bone density as a function of the starting density is relatively independent of such starting density (slight negative correlation).

TABLE 4

Patient Data [59]
TIME [Days]

| 1 | 1 | Pt | Age | 1st Date | Dens 1 | 2nd Date | Dens 2 | D/Ch 2-1 | Rel % Ch | Elap/T | Rank |
|---|---|----|----|----------|--------|----------|--------|----------|----------|--------|------|
| 2 | 61 | BM | 68.0 | 06/18/87 | 85.5 | 3/25/88 | 95.3 | 9.8 | 11.46% | 281 | 60 |
| 3 | 52 | CM | 39.0 | 04/06/87 | 82.9 | 2/20/88 | 85.7 | 2.8 | 3.38% | 320 | 51 |
| 4 | 49 | MB | 74.0 | 02/05/87 | 96.5 | 1/22/88 | 104.4 | 7.9 | 8.19% | 351 | 48 |
| 5 | 31 | FK | 71.6 | 12/11/85 | 79.0 | 1/16/87 | 101.4 | 22.4 | 28.35% | 401 | 30 |
| 6 | 4 | DR | 65.0 | 06/07/85 | 70.4 | 9/18/86 | 121.3 | 50.9 | 72.30% | 468 | 3 |
| 7 | 50 | TA | 59.0 | 11/20/86 | 94.0 | 3/7/88 | 104.3 | 10.3 | 10.96% | 473 | 49 |
| 8 | 22 | EL | 65.2 | 04/17/85 | 87.1 | 8/11/86 | 99.6 | 12.5 | 14.35% | 481 | 21 |
| 9 | 60 | JC | 30.0 | 11/06/86 | 90.4 | 3/24/88 | 95.0 | 4.6 | 5.09% | 504 | 59 |
| 10 | 37 | DS | 60.0 | 06/09/86 | 83.0 | 12/1/87 | 84.0 | 1.0 | 1.20% | 540 | 36 |
| 11 | 55 | JC | 63.0 | 09/15/86 | 98.4 | 3/23/88 | 108.8 | 10.4 | 10.57% | 555 | 54 |
| 12 | 10 | AM | 73.1 | 11/25/85 | 82.0 | 6/15/87 | 115.6 | 33.6 | 40.98% | 567 | 9 |
| 13 | 6 | JB | 74.0 | 04/04/86 | 69.0 | 11/10/87 | 108.9 | 39.9 | 57.83% | 585 | 5 |
| 14 | 7 | JS | 53.9 | 11/19/85 | 65.0 | 7/2/87 | 85.4 | 20.4 | 31.38% | 590 | 6 |
| 15 | 58 | EV | 74.0 | 08/06/86 | 72.4 | 3/19/88 | 76.6 | 4.2 | 5.80% | 591 | 57 |
| 16 | 59 | LP | 63.0 | 06/19/86 | 87.0 | 3/17/88 | 109.8 | 22.8 | 26.21% | 637 | 58 |
| 17 | 3 | RD | 66.7 | 11/06/84 | 85.6 | 8/8/86 | 119.4 | 33.8 | 39.49% | 640 | 2 |
| 18 | 34 | DB | 54.0 | 02/27/86 | 92.0 | 12/1/87 | 93.0 | 1.0 | 1.09% | 642 | 33 |
| 19 | 53 | LP | 73.3 | 04/15/86 | 81.0 | 2/20/88 | 115.2 | 34.2 | 42.22% | 676 | 52 |
| 20 | 15 | EH | 55.2 | 12/10/85 | 87.0 | 11/12/87 | 90.0 | 3.0 | 3.45% | 702 | 14 |
| 21 | 2 | JV | 55.0 | 01/03/85 | 98.7 | 12/8/86 | 105.7 | 7.0 | 7.09% | 704 | 1 |
| 22 | 35 | CB | 48.5 | 12/11/85 | 95.0 | 11/19/87 | 98.0 | 3.0 | 3.16% | 708 | 34 |
| 23 | 30 | CS | 73.1 | 03/27/85 | 85.8 | 3/25/87 | 91.9 | 6.1 | 7.11% | 728 | 29 |
| 24 | 14 | AM | 69.8 | 11/07/85 | 88.0 | 11/10/87 | 88.0 | .0 | .00% | 733 | 13 |
| 25 | 40 | SG | 65.9 | 12/13/85 | 88.0 | 1/6/88 | 112.7 | 24.7 | 28.07% | 754 | 39 |
| 26 | 8 | RW | 68.3 | 01/17/85 | 84.0 | 2/24/87 | 95.2 | 11.2 | 13.33% | 768 | 7 |
| 27 | 23 | LP | 48.5 | 01/29/85 | 93.1 | 3/9/87 | 128.5 | 35.4 | 38.02% | 769 | 22 |
| 28 | 25 | IS | 59.8 | 04/08/85 | 88.7 | 6/4/87 | 96.6 | 7.9 | 8.91% | 787 | 24 |
| 29 | 24 | AP | 60.0 | 01/10/85 | 84.0 | 3/10/87 | 120.4 | 36.4 | 43.33% | 789 | 23 |
| 30 | 45 | EJ | 61.4 | 12/05/85 | 80.0 | 2/5/88 | 89.5 | 9.5 | 11.88% | 792 | 44 |
| 31 | 57 | HN | 60.8 | 01/17/86 | 91.0 | 3/22/88 | 121.2 | 30.2 | 33.19% | 795 | 56 |
| 32 | 17 | MC | 63.5 | 08/28/85 | 91.0 | 11/3/87 | 94.0 | 3.0 | 3.30% | 797 | 16 |
| 33 | 29 | ID | 66.2 | 04/11/85 | 89.0 | 6/19/87 | 98.0 | 9.0 | 10.11% | 799 | 28 |
| 34 | 44 | JC | 56.3 | 11/20/85 | 89.0 | 2/5/88 | 106.6 | 17.6 | 19.78% | 807 | 43 |
| 35 | 54 | NF | 61.8 | 12/19/85 | 95.0 | 3/8/88 | 132.2 | 37.2 | 39.16% | 810 | 53 |
| 36 | 33 | FF | 64.9 | 03/25/85 | 88.7 | 6/16/87 | 103.5 | 14.8 | 16.69% | 813 | 32 |
| 37 | 20 | MB | 72.6 | 01/09/85 | 75.1 | 4/14/87 | 103.9 | 28.8 | 38.35% | 825 | 19 |
| 38 | 32 | GF | 60.0 | 01/18/85 | 113.2 | 4/29/87 | 128.1 | 14.9 | 13.16% | 831 | 31 |
| 39 | 42 | EW | 90.3 | 10/29/85 | 73.0 | 2/11/88 | 87.9 | 14.9 | 20.41% | 835 | 41 |
| 40 | 56 | AS | 67.1 | 11/05/85 | 89.0 | 3/23/88 | 107.5 | 18.5 | 20.79% | 869 | 55 |
| 41 | 26 | #IS | 60.0 | 10/18/84 | 69.0 | 3/24/87 | 106.9 | 37.9 | 54.93% | 887 | 25 |
| 42 | 27 | VB | 64.7 | 10/11/84 | 93.0 | 4/14/87 | 95.9 | 2.9 | 3.12% | 915 | 26 |
| 43 | 28 | MS | 55.3 | 03/07/85 | 76.8 | 10/23/87 | 89.6 | 12.8 | 16.67% | 960 | 27 |
| 44 | 12 | NC | 46.6 | 10/17/84 | 86.0 | 6/10/87 | 89.2 | 3.2 | 3.72% | 966 | 11 |
| 45 | 16 | AD | 62.4 | 02/11/85 | 85.0 | 10/13/87 | 86.0 | 1.0 | 1.18% | 974 | 15 |
| 46 | 11 | ED | 71.7 | 09/27/84 | 72.3 | 6/16/87 | 96.5 | 24.2 | 33.47% | 992 | 10 |
| 47 | 19 | #RA | 62.7 | 01/08/85 | 78.0 | 10/20/87 | 80.0 | 2.0 | 2.56% | 1015 | 18 |
| 48 | 9 | MS | 75.2 | 10/29/84 | 85.5 | 8/13/87 | 129.8 | 44.3 | 51.81% | 1018 | 8 |
| 49 | 5 | LG | 74.2 | 05/30/84 | 97.7 | 3/25/87 | 148.0 | 50.3 | 51.48% | 1029 | 4 |
| 50 | 46 | DC | 54.3 | 02/19/85 | 96.2 | 2/5/88 | 116.0 | 19.8 | 20.58% | 1081 | 45 |
| 51 | 43 | HA | 43.3 | 01/24/85 | 101.9 | 2/6/88 | 105.4 | 3.5 | 3.43% | 1108 | 42 |
| 52 | 18 | VB | 63.7 | 10/24/84 | 96.0 | 11/17/87 | 98.0 | 2.0 | 2.08% | 1119 | 17 |
| 53 | 39 | JG | 72.0 | 11/08/84 | 77.9 | 12/14/87 | 144.6 | 66.7 | 85.62% | 1131 | 38 |
| 54 | 13 | MD | 71.8 | 04/26/84 | 91.5 | 6/9/87 | 111.4 | 19.9 | 21.75% | 1139 | 12 |
| 55 | 21 | BB | 76.3 | 07/31/84 | 62.2 | 10/21/87 | 99.7 | 37.5 | 60.29% | 1177 | 20 |
| 56 | 38 | TC | 74.4 | 08/16/84 | 69.0 | 11/24/87 | 76.0 | 7.0 | 10.14% | 1195 | 37 |
| 57 | 47 | MM | 52.2 | 10/18/84 | 101.0 | 2/9/88 | 116.6 | 15.6 | 15.45% | 1209 | 46 |
| 58 | 36 | HG | 64.1 | 07/05/84 | 83.0 | 12/1/87 | 84.0 | 1.0 | 1.20% | 1244 | 35 |
| 59 | 51 | EM | 58.8 | 08/24/84 | 102.7 | 3/1/88 | 110.3 | 7.6 | 7.40% | 1285 | 50 |
| 60 | 41 | TW | 66.8 | 07/03/84 | 106.1 | 2/9/88 | 130.3 | 24.2 | 22.81% | 1316 | 40 |

TABLE 5

Patient Data [59]
Density #1

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | Rank |
| 2 | 21 | BB | 76.3 | 07/31/84 | 62.2 | 10/21/87 | 99.7 | 37.5 | 60.29% | 1177 | 20 |
| 3 | 7 | JS | 53.9 | 11/19/85 | 65.0 | 7/2/87 | 85.4 | 20.4 | 31.38% | 590 | 6 |
| 4 | 26 | #IS | 60.0 | 10/18/84 | 69.0 | 3/24/87 | 106.9 | 37.9 | 54.93% | 887 | 25 |
| 5 | 6 | JB | 74.0 | 04/04/86 | 69.0 | 11/10/87 | 108.9 | 39.9 | 57.83% | 585 | 5 |
| 6 | 38 | TC | 74.4 | 08/16/84 | 69.0 | 11/24/87 | 76.0 | 7.0 | 10.14% | 1195 | 37 |
| 7 | 4 | DR | 65.0 | 06/07/85 | 70.4 | 9/18/86 | 121.3 | 50.9 | 72.30% | 468 | 3 |

TABLE 5-continued

Patient Data [59]
Density #1

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | Rank |
| 8 | 11 | ED | 71.7 | 09/27/84 | 72.3 | 6/16/87 | 96.5 | 24.2 | 33.47% | 992 | 10 |
| 9 | 58 | EV | 74.0 | 08/06/86 | 72.4 | 3/19/88 | 76.6 | 4.2 | 5.80% | 591 | 57 |
| 10 | 42 | EW | 90.3 | 10/29/85 | 73.0 | 2/11/88 | 87.9 | 14.9 | 20.41% | 835 | 41 |
| 11 | 20 | MB | 72.6 | 01/09/85 | 75.1 | 4/14/87 | 103.9 | 28.8 | 38.35% | 825 | 19 |
| 12 | 28 | MS | 55.3 | 03/07/85 | 76.8 | 10/23/87 | 89.6 | 12.8 | 16.67% | 960 | 27 |
| 13 | 39 | JG | 72.0 | 11/08/84 | 77.9 | 12/14/87 | 144.6 | 66.7 | 85.62% | 1131 | 38 |
| 14 | 19 | #RA | 62.7 | 01/08/85 | 78.0 | 10/20/87 | 80.0 | 2.0 | 2.56% | 1015 | 18 |
| 15 | 31 | FK | 71.6 | 12/11/85 | 79.0 | 1/16/87 | 101.4 | 22.4 | 28.35% | 401 | 30 |
| 16 | 45 | EJ | 61.4 | 12/05/85 | 80.0 | 2/5/88 | 89.5 | 9.5 | 11.88% | 792 | 44 |
| 17 | 53 | LP | 73.3 | 04/15/86 | 81.0 | 2/20/88 | 115.2 | 34.2 | 42.22% | 676 | 52 |
| 18 | 10 | AM | 73.1 | 11/25/85 | 82.0 | 6/15/87 | 115.6 | 33.6 | 40.98% | 567 | 9 |
| 19 | 52 | CM | 39.0 | 04/06/87 | 82.9 | 2/20/88 | 85.7 | 2.8 | 3.38% | 320 | 51 |
| 20 | 37 | DS | 60.0 | 06/09/86 | 83.0 | 12/1/87 | 84.0 | 1.0 | 1.20% | 540 | 36 |
| 21 | 36 | HG | 64.1 | 07/05/84 | 83.0 | 12/1/87 | 84.0 | 1.0 | 1.20% | 1244 | 35 |
| 22 | 24 | AP | 60.0 | 01/10/85 | 84.0 | 3/10/87 | 120.4 | 36.4 | 43.33% | 789 | 23 |
| 23 | 8 | RW | 68.3 | 01/17/85 | 84.0 | 2/24/87 | 95.2 | 11.2 | 13.33% | 768 | 7 |
| 24 | 16 | AD | 62.4 | 02/11/85 | 85.0 | 10/13/87 | 86.0 | 1.0 | 1.18% | 974 | 15 |
| 25 | 61 | BM | 68.0 | 06/18/87 | 85.5 | 3/25/88 | 95.3 | 9.8 | 11.46% | 281 | 60 |
| 26 | 9 | MS | 75.2 | 10/29/84 | 85.5 | 8/13/87 | 129.8 | 44.3 | 51.81% | 1018 | 8 |
| 27 | 3 | RD | 66.7 | 11/06/84 | 85.6 | 8/8/86 | 119.4 | 33.8 | 39.49% | 640 | 2 |
| 28 | 30 | CS | 73.1 | 03/27/85 | 85.8 | 3/25/87 | 91.9 | 6.1 | 7.11% | 728 | 29 |
| 29 | 12 | NC | 46.6 | 10/17/84 | 86.0 | 6/10/87 | 89.2 | 3.2 | 3.72% | 966 | 11 |
| 30 | 15 | EH | 55.2 | 12/10/85 | 87.0 | 11/12/87 | 90.0 | 3.0 | 3.45% | 702 | 14 |
| 31 | 59 | LP | 63.0 | 06/19/86 | 87.0 | 3/17/88 | 109.8 | 22.8 | 26.21% | 637 | 58 |
| 32 | 22 | EL | 65.2 | 04/17/85 | 87.1 | 8/11/86 | 99.6 | 12.5 | 14.35% | 481 | 21 |
| 33 | 40 | SG | 65.9 | 12/13/85 | 88.0 | 1/6/88 | 112.7 | 24.7 | 28.07% | 754 | 39 |
| 34 | 14 | AM | 69.8 | 11/07/85 | 88.0 | 11/10/87 | 88.0 | .0 | .00% | 733 | 13 |
| 35 | 25 | IS | 59.8 | 04/08/85 | 88.7 | 6/4/87 | 96.6 | 7.9 | 8.91% | 787 | 24 |
| 36 | 33 | FF | 64.9 | 03/25/85 | 88.7 | 6/16/87 | 103.5 | 14.8 | 16.69% | 813 | 32 |
| 37 | 44 | JC | 56.3 | 11/20/85 | 89.0 | 2/5/88 | 106.6 | 17.6 | 19.78% | 807 | 43 |
| 38 | 29 | ID | 66.2 | 04/11/85 | 89.0 | 6/19/87 | 98.0 | 9.0 | 10.11% | 799 | 28 |
| 39 | 56 | AS | 67.1 | 11/05/85 | 89.0 | 3/23/88 | 107.5 | 18.5 | 20.79% | 869 | 55 |
| 40 | 60 | JC | 30.0 | 11/06/86 | 90.4 | 3/24/88 | 95.0 | 4.6 | 5.09% | 504 | 59 |
| 41 | 57 | HN | 60.8 | 01/17/86 | 91.0 | 3/22/88 | 121.2 | 30.2 | 33.19% | 795 | 56 |
| 42 | 17 | MC | 63.5 | 08/28/85 | 91.0 | 11/3/87 | 94.0 | 3.0 | 3.30% | 797 | 16 |
| 43 | 13 | MD | 71.8 | 04/26/84 | 91.5 | 6/9/87 | 111.4 | 19.9 | 21.75% | 1139 | 12 |
| 44 | 34 | DB | 54.0 | 02/27/86 | 92.0 | 12/1/87 | 93.0 | 1.0 | 1.09% | 642 | 33 |
| 45 | 27 | VB | 64.7 | 10/11/84 | 93.0 | 4/14/87 | 95.9 | 2.9 | 3.12% | 915 | 26 |
| 46 | 23 | LP | 48.5 | 01/29/85 | 93.1 | 3/9/87 | 128.5 | 35.4 | 38.02% | 769 | 22 |
| 47 | 50 | TA | 59.0 | 11/20/86 | 94.0 | 3/7/88 | 104.3 | 10.3 | 10.96% | 473 | 49 |
| 48 | 35 | CB | 48.5 | 12/11/85 | 95.0 | 11/19/87 | 98.0 | 3.0 | 3.16% | 708 | 34 |
| 49 | 54 | NF | 61.8 | 12/19/85 | 95.0 | 3/8/88 | 132.2 | 37.2 | 39.16% | 810 | 53 |
| 50 | 18 | VB | 63.7 | 10/24/84 | 96.0 | 11/17/87 | 98.0 | 2.0 | 2.08% | 1119 | 17 |
| 51 | 46 | DC | 54.3 | 02/19/85 | 96.2 | 2/5/88 | 116.0 | 19.8 | 20.58% | 1081 | 45 |
| 52 | 49 | MB | 74.0 | 02/05/87 | 96.5 | 1/22/88 | 104.4 | 7.9 | 8.19% | 351 | 48 |
| 53 | 5 | LG | 74.2 | 05/30/84 | 97.7 | 3/25/87 | 148.0 | 50.3 | 51.48% | 1029 | 4 |
| 54 | 55 | JC | 63.0 | 09/15/86 | 98.4 | 3/23/88 | 108.8 | 10.4 | 10.57% | 555 | 54 |
| 55 | 2 | JV | 55.0 | 01/03/85 | 98.7 | 12/8/86 | 105.7 | 7.0 | 7.09% | 704 | 1 |
| 56 | 47 | MM | 52.2 | 10/18/84 | 101.0 | 2/9/88 | 116.6 | 15.6 | 15.45% | 1209 | 46 |
| 57 | 43 | HA | 43.3 | 01/24/85 | 101.9 | 2/6/88 | 105.4 | 3.5 | 3.43% | 1108 | 42 |
| 58 | 51 | EM | 58.8 | 08/24/84 | 102.7 | 3/1/88 | 110.3 | 7.6 | 7.40% | 1285 | 50 |
| 59 | 41 | TW | 66.8 | 07/03/84 | 106.1 | 2/9/88 | 130.3 | 24.2 | 22.81% | 1316 | 40 |
| 60 | 32 | GF | 60.0 | 01/18/85 | 113.2 | 4/29/87 | 128.1 | 14.9 | 13.16% | 831 | 31 |
| 61 | | | 63.2 | | 86.4 | | 104.0 | 17.6 | 21.35% | 804.69 | |

TABLE 6

Patient Data [59]
Density #2

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | Rank |
| 2 | 38 | TC | 74.4 | 08/16/84 | 69.0 | 11/24/87 | 76.0 | 7.0 | 10.14% | 1195 | 37 |
| 3 | 58 | EV | 74.0 | 08/06/86 | 72.4 | 3/19/88 | 76.6 | 4.2 | 5.80% | 591 | 57 |
| 4 | 19 | #RA | 62.7 | 01/08/85 | 78.0 | 10/20/87 | 80.0 | 2.0 | 2.56% | 1015 | 18 |
| 5 | 37 | DS | 60.0 | 06/09/86 | 83.0 | 12/1/87 | 84.0 | 1.0 | 1.20% | 540 | 36 |
| 6 | 36 | HG | 64.1 | 07/05/84 | 83.0 | 12/1/87 | 84.0 | 1.0 | 1.20% | 1244 | 35 |
| 7 | 7 | JS | 53.9 | 11/19/85 | 65.0 | 7/2/87 | 85.4 | 20.4 | 31.38% | 590 | 6 |
| 8 | 52 | CM | 39.0 | 04/06/87 | 82.9 | 2/20/88 | 85.7 | 2.8 | 3.38% | 320 | 51 |
| 9 | 16 | AD | 62.4 | 02/11/85 | 85.0 | 10/13/87 | 86.0 | 1.0 | 1.18% | 974 | 15 |
| 10 | 42 | EW | 90.3 | 10/29/85 | 73.0 | 2/11/88 | 87.9 | 14.9 | 20.41% | 835 | 41 |
| 11 | 14 | AM | 69.8 | 11/07/85 | 88.0 | 11/10/87 | 88.0 | .0 | .00% | 733 | 13 |
| 12 | 12 | NC | 46.6 | 10/17/84 | 86.0 | 6/10/87 | 89.2 | 3.2 | 3.72% | 966 | 11 |
| 13 | 45 | EJ | 61.4 | 12/05/85 | 80.0 | 2/5/88 | 89.5 | 9.5 | 11.88% | 792 | 44 |
| 14 | 28 | MS | 55.3 | 03/07/85 | 76.8 | 10/23/87 | 89.6 | 12.8 | 16.67% | 960 | 27 |
| 15 | 15 | EH | 55.2 | 12/10/85 | 87.0 | 11/12/87 | 90.0 | 3.0 | 3.45% | 702 | 14 |
| 16 | 30 | CS | 73.1 | 03/27/85 | 85.8 | 3/25/87 | 91.9 | 6.1 | 7.11% | 728 | 29 |

TABLE 6-continued

Patient Data [59]
Density #2

| | A | B | C | D | E | F | G | H | I | J | K |
|---|---|---|---|---|---|---|---|---|---|---|---|
| 1 | 1 | Pt | Age | 1st Date | Dens 1 | 2nd Date | Dens 2 | D/Ch 2-1 | Rel % Ch | Elap/T | Rank |
| 17 | 34 | DB | 54.0 | 02/27/86 | 92.0 | 12/1/87 | 93.0 | 1.0 | 1.09% | 642 | 33 |
| 18 | 17 | MC | 63.5 | 08/28/85 | 91.0 | 11/3/87 | 94.0 | 3.0 | 3.30% | 797 | 16 |
| 19 | 60 | JC | 30.0 | 11/06/86 | 90.4 | 3/24/88 | 95.0 | 4.6 | 5.09% | 504 | 59 |
| 20 | 8 | RW | 68.3 | 01/17/85 | 84.0 | 2/24/87 | 95.2 | 11.2 | 13.33% | 768 | 7 |
| 21 | 61 | BM | 68.0 | 06/18/87 | 85.5 | 3/25/88 | 95.3 | 9.8 | 11.46% | 281 | 60 |
| 22 | 27 | VB | 64.7 | 10/11/84 | 93.0 | 4/14/87 | 95.9 | 2.9 | 3.12% | 915 | 26 |
| 23 | 11 | ED | 71.7 | 09/27/84 | 72.3 | 6/16/87 | 96.5 | 24.2 | 33.47% | 992 | 10 |
| 24 | 25 | IS | 59.8 | 04/08/85 | 88.7 | 6/4/87 | 96.6 | 7.9 | 8.91% | 787 | 24 |
| 25 | 35 | CB | 48.5 | 12/11/85 | 95.0 | 11/19/87 | 98.0 | 3.0 | 3.16% | 708 | 34 |
| 26 | 18 | VB | 63.7 | 10/24/84 | 96.0 | 11/17/87 | 98.0 | 2.0 | 2.08% | 1119 | 17 |
| 27 | 29 | ID | 66.2 | 04/11/85 | 89.0 | 6/19/87 | 98.0 | 9.0 | 10.11% | 799 | 28 |
| 28 | 22 | EL | 65.2 | 04/17/85 | 87.1 | 8/11/86 | 99.6 | 12.5 | 14.35% | 481 | 21 |
| 29 | 21 | BB | 76.3 | 07/31/84 | 62.2 | 10/21/87 | 99.7 | 37.5 | 60.29% | 1177 | 20 |
| 30 | 31 | FK | 71.6 | 12/11/85 | 79.0 | 1/16/87 | 101.4 | 22.4 | 28.35% | 401 | 30 |
| 31 | 33 | FF | 64.9 | 03/25/85 | 88.7 | 6/16/87 | 103.5 | 14.8 | 16.69% | 813 | 32 |
| 32 | 20 | MB | 72.6 | 01/09/85 | 75.1 | 4/14/87 | 103.9 | 28.8 | 38.35% | 825 | 19 |
| 33 | 50 | TA | 59.0 | 11/20/86 | 94.0 | 3/7/88 | 104.3 | 10.3 | 10.96% | 473 | 49 |
| 34 | 49 | MB | 74.0 | 02/05/87 | 96.5 | 1/22/88 | 104.4 | 7.9 | 8.19% | 351 | 48 |
| 35 | 43 | HA | 43.3 | 01/24/85 | 101.9 | 2/6/88 | 105.4 | 3.5 | 3.43% | 1108 | 42 |
| 36 | 2 | JV | 55.0 | 01/03/85 | 98.7 | 12/8/86 | 105.7 | 7.0 | 7.09% | 704 | 1 |
| 37 | 44 | JC | 56.3 | 11/20/85 | 89.0 | 2/5/88 | 106.6 | 17.6 | 19.78% | 807 | 43 |
| 38 | 26 | #IS | 60.0 | 10/18/84 | 69.0 | 3/24/87 | 106.9 | 37.9 | 54.93% | 887 | 25 |
| 39 | 56 | AC | 67.1 | 11/05/85 | 89.0 | 3/23/88 | 107.5 | 18.5 | 20.79% | 869 | 55 |
| 40 | 55 | JC | 63.0 | 09/15/86 | 98.4 | 3/23/88 | 108.8 | 10.4 | 10.57% | 555 | 54 |
| 41 | 6 | JB | 74.0 | 04/04/86 | 69.0 | 11/10/87 | 108.9 | 39.9 | 57.83% | 585 | 5 |
| 42 | 59 | LP | 63.0 | 06/19/86 | 87.0 | 3/17/88 | 109.8 | 22.8 | 26.21% | 637 | 58 |
| 43 | 51 | EM | 58.8 | 08/24/84 | 102.7 | 3/1/88 | 110.3 | 7.6 | 7.40% | 1285 | 50 |
| 44 | 13 | MD | 71.8 | 04/26/84 | 91.5 | 6/9/87 | 111.4 | 19.9 | 21.75% | 1139 | 12 |
| 45 | 40 | SG | 65.9 | 12/13/85 | 88.0 | 1/6/88 | 112.7 | 24.7 | 28.07% | 754 | 39 |
| 46 | 53 | LP | 73.3 | 04/15/86 | 81.0 | 2/20/88 | 115.2 | 34.2 | 42.22% | 676 | 52 |
| 47 | 10 | AM | 73.1 | 11/25/85 | 82.0 | 6/15/87 | 115.6 | 33.6 | 40.98% | 567 | 9 |
| 48 | 46 | DC | 54.3 | 02/19/85 | 96.2 | 2/5/88 | 116.0 | 19.8 | 20.58% | 1081 | 45 |
| 49 | 47 | MM | 52.2 | 10/18/84 | 101.0 | 2/9/88 | 116.6 | 15.6 | 15.45% | 1209 | 46 |
| 50 | 3 | RD | 66.7 | 11/06/84 | 85.6 | 8/8/86 | 119.4 | 33.8 | 39.49% | 640 | 2 |
| 51 | 24 | AP | 60.0 | 01/10/85 | 84.0 | 3/10/87 | 120.4 | 36.4 | 43.33% | 789 | 23 |
| 52 | 57 | HN | 60.8 | 01/17/86 | 91.0 | 3/22/88 | 121.2 | 30.2 | 33.19% | 795 | 56 |
| 53 | 4 | DR | 65.0 | 06/07/85 | 70.4 | 9/18/86 | 121.3 | 50.9 | 72.30% | 468 | 3 |
| 54 | 32 | GF | 60.0 | 01/18/85 | 113.2 | 4/29/87 | 128.1 | 14.9 | 13.16% | 831 | 31 |
| 55 | 23 | LP | 48.5 | 01/29/85 | 93.1 | 3/9/87 | 128.5 | 35.4 | 38.02% | 769 | 22 |
| 56 | 9 | MS | 75.2 | 10/29/84 | 85.5 | 8/13/87 | 129.8 | 44.3 | 51.81% | 1018 | 8 |
| 57 | 41 | TW | 66.8 | 07/03/84 | 106.1 | 2/9/88 | 130.3 | 24.2 | 22.81% | 1316 | 40 |
| 58 | 54 | NF | 61.8 | 12/19/85 | 95.0 | 3/8/88 | 132.2 | 37.2 | 39.16% | 810 | 53 |
| 59 | 39 | JG | 72.0 | 11/08/84 | 77.9 | 12/14/87 | 144.6 | 66.7 | 85.62% | 1131 | 38 |
| 60 | 5 | LG | 74.2 | 05/30/84 | 97.7 | 3/25/87 | 148.0 | 50.3 | 51.48% | 1029 | 4 |
| 61 | | | 63.2 | | 86.4 | | 104.0 | 17.6 | 21.35% | 804.69 | |

Table 6 presents the data from Table 2 sorted by ascending ending density. FIGS. 13 and 14 corresponding to this data arrangement show that there is a positive correlation between the ending density and the amount of density change.

FIGS. 15 and 16 based upon Table 4, illustrate the patient's ending bone density as a function of ascending elapsed time on the regimen. It is apparent from FIG. 16 that there is a positive correlation between the length of time on the regimen and the ending density of the patient.

From the data presented and its analysis, it is clear that compliant use of this regimen generally results in an increase in bone density regardless of the age of the patient.

This data can further be analyzed based upon the known bone loss for post-menopausal women as discussed earlier to ascertain if this test data is statistically significant in showing that there is an improvement in bone density for patients using the regimen. This statistical analysis assumes that there is an equal probability that a patient will have increased bone density at the time of the second measurement as the probability that the patient will have decreased bone density at the time of the second measurement. Such an assumption is overly optimistic because the medical literature clearly shows that post-menopausal women typically have lower bone density over time and therefore the probability of bone density increasing at the time of the second measurement is actually less than fifty percent.

Thus for the sixty-three patients on whom test results have been obtained to date, sixty-three were compliant and not simultaneously receiving contraindicating drugs. Of these sixty-three patients, all but one showed an increase in relative bone density between the first measurement and the second measurement.

Assuming the probability of obtaining increased bone density on the second measurement to be fifty percent, then the probability of fifty-eight patients showing an increase in bone density would be, due to chance alone, is equal to approximately $(0.5)^{58}$ (that is the 50 percent probability of finding an increase in bone density per patient raised to the 63rd power). This number is approximately zero. This result is analogous to the probability of obtaining fifty-eight heads for sixty-three consecutive flips of a coin which, as is intuitively clear, is a virtual impossibility.

Therefore, the probability of fifty-eight patients having a higher bone density measurement for the second measurement if due to chance is virtually zero. The fact that fifty-eight out of sixty-three patients show an increase in bone density is highly statistically significant.

From the foregoing, it can be concluded that patients who comply with the regimen according to the present invention have a statistically significant chance of increasing their bone density over patients who do not undergo such a regimen. Furthermore, the sample of sixty-three patients out of a total population of seventy-nine patients selected for the study is statistically significant since it is nearly three-quarters of the total number of patients in the study.

For all the foregoing reasons, it is submitted that the evidence supports the conclusion that the data represents a statistically significant finding that the calendar oriented use of an estrogen, progesterone and calcium regimen as defined above results in increase of bone density in post-menopausal women.

It will thus be seen that the object set forth above, and those made apparent from the preceding description, are efficiently attained, and since certain changes may be made in carrying out the above process without departing from the scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

TABLE 11

FOOTNOTES

1. Utian W H. Overview on menopause.
   Am J Obstet Gynecol. 1987; 56: 1280–1283.
2. Ettinger B. Overview of the efficacy of hormonal replacement therapy. Am J Obstet Gynecol 1987; 56: 1298–303.
3. Riggs B L. Pathogenesis of osteoporosis. Am J Obstet Gynecol 1987; 56: 1342–46.
4. Judd H, Utian W H. Current perspectives in the management of the menopausal and postmenopausal patient - Introduction: what we hope to learn. Am J Obstet Gynecol 1987; 56: 1279–80.
5. Lindsay R. Estrogen therapy in the prevention and management of osteoporosis. Am J Obstet Gynecol 1987; 56: 1347–51.
6. Parfitt A M. Quantum concept of bone remodeling and turnover: implications for the pathogenesis of osteoporosis. Calcif Tissue Int 1979; 28: 1–5.
7. Lindsay R, Aitken J M, Anderson J B, Hart D M, MacDonald E B, Clark A C. Long-term prevention of post-menopausal osteoporosis by estrogen. Lancet 1976; 1: 1038–41.
8. Lindsay R, Hart D M, Forrest C, Baird C. Prevention of spinal osteoporosis in oophorectomized women. Lancet 1980; 2: 1151–4.
9. Ravnikar V A. Compliance with hormone therapy. Am J Obstet Gynecol 1987; 56: 1332–34.
10. Genant H K, Cann C E, Ettinger B, Gordon G S. Quantitative computed tomography of vertebral spongiosa: a sensitive method for detecting early bone loss after oophorectomy. Ann Intern Med 1982; 97: 699–705.
11. Kolata G. How important is dietary calcium in preventing osteoporsis? Science 1986; 233: 519–20.
12. Barnes D M. Close encounters with an osteoclaust. Science 1987; 236: 914–16.
13. Peck W A, Riggs B L, Bell N H. Physician's resource manual on osteoporosis. Nat Osteoporosis Found. 1987: 15–16.
14. Reinbold W D, Genant H K, Reiser U J, Harris, S T, Ettinger B. Bone mineral content in early-post-menopausal and postmenopausal osteoporotic women: comparison of measurement methods. Radiol 1986; 160: 469–78
15. Weissman B N. Women's health: osteoporosis: radiologic and nuclear medicine procedures. Nat Con on Women's Health, U.S. Dept. of Health and Human Services. July, 1986: 127–31.

TABLE 11-continued

FOOTNOTES

16. Ott S M, Chesnut III C H, Hanson J A, Kilcoyne R F, Murano R, Lewellen T K. Comparison of bone mass measurements using different diagnostic techniques in patients with postmenopausal osteoporosis. Osteoporosis: Proc Copenhagan Int Sym on Osteoporosis 1984; June 3–8; 93–6.

Having described the invention what is claimed is:

1. A method of increasing the bone density in a post-menopausal woman as well as retarding the effects of osteoporosis and treating the symptoms of menopause regardless of the age of the post-menopausal woman at the time the method is initiated, comprising the steps of
   (1) compliantly ingesting an effective daily dose amount of estrogen hormone for each of calendar days 1 through 25 of each calendar month;
   (2) compliantly ingesting an effective daily does amount of progesterone hormone for each of calendar days 16 through 25 of each calendar month;
   (3) compliantly ingesting an effective daily dose amount of non-dietary calcium for at least calendar days 26 through the remaining days of the calendar month; said effective daily does amount of calcium being independent of consumption of dietary calcium at any intake level; and
   (4) repeating the regimen of steps 1 through 3 for each consecutive calendar month thereafter.

2. A method of increasing bone density in a post-menopausal woman as defined in claim 1, wherein the estrogen comprises conjugated estrogens.

3. A method of increasing bone density in a post-menopausal woman as defined in claim 2, wherein the progesterone hormone comprises medroxyprogesterone acetate.

4. A method of increasing bone density in a post-menopausal woman as defined in claim 3, wherein the calcium comprises calcium carbonate.

5. A method of increasing bone density in a post-menopausal woman as defined in claim 4, wherein the conjugated estrogens are in the daily dosage amount of 0.625 mg.

6. A method of increasing bone density in a post-menopausal women as defined in claim 5, wherein the medroxyprogesterone acetate comprises a daily dose of 10 mg.

7. A method of increasing bone density in a post-menopausal woman as defined in claim 6, wherein the calcium carbonate comprises a daily dose of 500 mg.

8. A method of increasing bone density in a post-menopausal woman as defined in claim 1, wherein the estrogen is in the daily dosage amount of 0.625 mg., the progesterone is in a daily dosage amount of 10 mg. and the calcium is in a daily dosage amount of 500 mg.

9. A method of increasing bone density in a post-menopausal woman as defined in claim 1, wherein the progesterone hormone comprises medroxyprogesterone acetate.

10. A method of increasing bone density in a post-menopausal woman as defined in claim 9, wherein the medroxyprogesterone acetate comprises a daily does of 10 mg.

11. A method of increasing bone density in a post-menopausal woman as defined in claim 2, wherein the conjugated estrogens are in the daily dosage amount of 0.625 mg.

12. A method of increasing bone density in a post-menopausal woman as defined in claim 1, wherein the calcium comprise calcium carbonate.

13. A method of increasing bone density in a post-menopausal woman as defined in claim 12, wherein the calcium carbonate comprises a daily dose of 500 mg.

14. A method of increasing the bone density in a post-menopausal woman as well as retarding the effects of osteoporosis and treating the symptoms of menopause regardless of the age of the post-menopausal woman at the time the method is initiated, comprising the steps of
   (1) compliantly ingesting an effective daily dose amount of estrogen hormone for each of at least calendar days 1-25 of each calendar month;
   (2) compliantly ingesting an effective daily dose amount of progesterone hormone for each of at least calendar days 16-25 of each calendar month;
   (3) compliantly ingesting an effective daily dose amount of non-dietary calcium for each of at least calendar days 26 through the remaining days of the calendar month; said effective daily dose amount of calcium being independent of consumption of dietary calcium at any intake level; and
   (4) repeating the regimen of steps 1 through 3 for each consecutive calendar month thereafter.

15. A method of increasing bone density in a post-menopausal woman as defined in claim 14, wherein the estrogen comprises conjugated estrogens.

16. A method of increasing bone density in a post-menopausal woman as defined in claim 15, wherein the progesterone hormone comprises medroxyprogesterone acetate.

17. A method of increasing bone density in a post-menopausal woman as defined in claim 16, wherein the calcium comprises calcium carbonate.

18. A method of increasing bone density in a post-menopausal woman as defined in claim 17, wherein the conjugated estrogens are in the daily dosage amount of 0.625 mg.

19. A method of increasing bone density in a post-menopausal woman as defined in claim 18, wherein the medroxyprogesterone acetate comprises a daily dose of 10 mg.

20. A method of increasing bone density in a post-menopausal woman as defined in claim 19, wherein the calcium carbonate comprises a daily dose of 500 mg.

21. A method of increasing bone density in a post-menopausal woman as defined in claim 14, wherein the estrogen is in the daily dosage amount of 0.625 mg., the progesterone is in a daily dosage amount of 10 mg. and the calcium is in a daily dosage amount of 500 mg.

22. A method of increasing bone density in a post-menopausal woman as defined in claim 14, wherein the progesterone hormone comprises medroxyprogesterone acetate.

23. A method of increasing bone density in a post-menopausal woman as defined in claim 22, wherein the medroxyprogesterone acetate comprises a daily dose of 10 mg.

24. A method of increasing bone density in a post-menopausal woman as defined in claim 15, wherein the conjugated estrogens are in the daily dosage amount of 0.625 mg.

25. A method of increasing bone density in a post-menopausal woman as defined in claim 12, wherein the calcium comprises calcium carbonate.

26. A method of increasing bone density in a post-menopausal woman as defined in claim 25, wherein the calcium carbonate comprises a daily dose of 500 mg.

* * * * *